(12) United States Patent
Shigeta

(10) Patent No.: US 11,998,165 B2
(45) Date of Patent: Jun. 4, 2024

(54) IMAGE PROCESSING DEVICE AND METHOD OF OPERATING SAME

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 55 days.

(21) Appl. No.: 18/046,793

(22) Filed: Oct. 14, 2022

(65) Prior Publication Data

US 2023/0063128 A1 Mar. 2, 2023

Related U.S. Application Data

(63) Continuation of application No. PCT/JP2021/010862, filed on Mar. 17, 2021.

(30) Foreign Application Priority Data

Apr. 17, 2020 (JP) ................. 2020-074231

(51) Int. Cl.
*A61B 1/00* (2006.01)
*A61B 1/06* (2006.01)

(52) U.S. Cl.
CPC ............ *A61B 1/00009* (2013.01); *A61B 1/06* (2013.01)

(58) Field of Classification Search
CPC . A61B 1/000094; A61B 1/00009; A61B 1/06; A61B 1/0655; G06T 11/001; G16H 20/40; G16H 30/20; G16H 30/40; G16H 40/63
USPC .............................................. 348/65, 45, 71
See application file for complete search history.

(56) References Cited

U.S. PATENT DOCUMENTS

| | | |
|---|---|---|
| 2011/0230715 A1 | 9/2011 | Saito |
| 2012/0157768 A1 | 6/2012 | Saito |
| 2013/0030268 A1 | 1/2013 | Saito |
| 2014/0184769 A1 | 7/2014 | Ishihara et al. |
| 2015/0201871 A1 | 7/2015 | Shiraishi |

(Continued)

FOREIGN PATENT DOCUMENTS

| | | |
|---|---|---|
| EP | 2 912 990 A1 | 9/2015 |
| JP | 2007-215927 A | 8/2007 |

(Continued)

OTHER PUBLICATIONS

International Search Report issued in PCT/JP2021/010862; dated Jun. 8, 2021.

(Continued)

*Primary Examiner* — Sherrie Hsia
(74) *Attorney, Agent, or Firm* — Studebaker & Brackett PC

(57) ABSTRACT

An image processing device including an image processor, which acquires an endoscopic image, calculates biological information on the basis of the endoscopic image, sets a reference value of the biological information, generates a biological information image obtained by forming the biological information as an image so that a low value region equal to or lower than the reference value and the other region are distinguishable from each other, determines that the reference value is not appropriate in a case where a quasi-low value region in which the biological information is higher than the reference value and equal to or lower than a preset set value is present in the biological information image, and performs a notification regarding the reference value.

16 Claims, 19 Drawing Sheets

(56) References Cited

U.S. PATENT DOCUMENTS

2018/0368658 A1* 12/2018 Yamamoto ......... A61B 1/00163
2020/0402235 A1  12/2020 Shigeta et al.

FOREIGN PATENT DOCUMENTS

| JP | 2011-194028 A  | 10/2011 |
| JP | 2012-139482 A  | 7/2012  |
| JP | 2015-136397 A  | 7/2015  |
| WO | 2013/035738 A1 | 3/2013  |
| WO | 2019/172231 A1 | 9/2019  |

OTHER PUBLICATIONS

International Preliminary Report on Patentability (Chapter I) and Written Opinion of the International Searching Authority issued in PCT/JP2021/010862; dated Oct. 13, 2022.

The extended European search report issued by the European Patent Office dated Oct. 12, 2023, which corresponds to European Patent Application No. 21787780.2-1210 and is related to U.S. Appl. No. 18/046,793.

* cited by examiner

DETERMINATION:
(A): REFERENCE VALUE IS APPROPRIATE
(B): REFERENCE VALUE IS APPROPRIATE
(C): REFERENCE VALUE IS NOT APPROPRIATE

DETERMINATION: REFERENCE VALUE IS NOT APPROPRIATE

IMAGE PROCESSING DEVICE AND METHOD OF OPERATING SAME

CROSS-REFERENCE TO RELATED APPLICATIONS

This application is a Continuation of PCT International Application No. PCT/JP2021/010862 filed on 17 Mar. 2021, which claims priority under 35 U.S.C § 119(a) to Japanese Patent Application No. 2020-074231 filed on 17 Apr. 2020. The above application is hereby expressly incorporated by reference, in its entirety, into the present application.

BACKGROUND OF THE INVENTION

1. Field of the Invention

The present invention relates to an image processing device that performs image processing by using a medical image such as an endoscopic image and a method of operating the same.

2. Description of the Related Art

In the medical field, examinations using endoscope systems are becoming widespread. The endoscope systems comprise, for example, an endoscope (referred to as scope) inserted into a subject, a light source device that generates illumination light for illuminating the subject, and a processor device that acquires an endoscopic image of the subject by using the endoscope, a display that displays the endoscopic image or the like, and the like.

Additionally, in recent years, endoscope systems that calculate and display biological information of a subject by using an endoscopic image have been known. In that case, it is known that the biological information is calculated and displayed as a relative value. For example, an electronic endoscope system that calculates a reference value of blood vessel information on the basis of the image data of a set reference value region and displays the blood vessel information of an endoscopic image as a relative value using the reference value in pseudo color is known (JP2011-194028A, corresponding to US2011/0230715A1). In addition, an endoscope system that calculates the reliability of biological information on the basis of an image, sets a reference value that serves as a reference for biological information by using the reliability, and generates a difference image on the basis of a difference value between a measured value and the reference value is known (WO2019/172231A1). Additionally, there is known an endoscope system that displays a region having a particularly low oxygen saturation in a color different from a normal color by image processing of an endoscopic image (JP2012-139482A, corresponding to US2012/0157768A1).

SUMMARY OF THE INVENTION

In a case where the biological information such as the oxygen saturation is displayed, the reference value of the biological information is set, and the biological information is calculated and displayed as a relative value. Accordingly, a specific portion of the biological information can be identified easily. In this way, there is an advantage in using the reference value in the biological information. On the other hand, however, in a case where a plurality of sites are observed or in a situation where the biological information changes over time even in the same site, the same reference value continues to be used. Accordingly, inconvenience may occur.

By continuing using the same reference value, for example, in the examination of the oxygen saturation in which the oxygen saturation is formed as an image and displayed, a problem may occur in a case where a region in which the oxygen saturation is specific is identified. In order to make it easier to recognize a low oxygen region where the oxygen saturation is particularly low, it is assumed that the reference value of the oxygen saturation is set to be particularly low and the low oxygen region equal to or lower than the reference value is displayed by an image. Then, in a case where the oxygen saturation of another site or the same site after the elapse of time is examined without changing the reference value, the low oxygen region may be no longer present in the subject. In this case, the low oxygen region is not displayed. However, even in a case where the low oxygen region is not displayed, there is a case where a quasi-low oxygen region that is slightly higher than the reference value but is generally regarded as the low oxygen region is actually present. There is a possibility that both the low oxygen region and the quasi-low oxygen region are regions in which the oxygen saturation is specific, and are lesions, suture failures or the like of the intestinal tract or the like. There may be a problem that doctors or the like are not aware of the presence of a region having a specific oxygen saturation.

An object of the present invention is to provide an image processing device and a method of operating the image processing device, which can prevent overlooking of a portion where biological information is specific.

The image processing device of the present invention comprises an image processor. The image processor acquires an endoscopic image obtained by imaging a subject with an endoscope, calculates biological information on the basis of the endoscopic image, sets a reference value of the biological information, generates a biological information image obtained by forming the biological information as an image so that a low value region equal to or lower than the reference value and the other region are distinguishable from each other, generates a display image in which the biological information image is superimposed on the endoscopic image, determines that the reference value is not appropriate in a case where a quasi-low value region in which the biological information is higher than the reference value and equal to or lower than a preset set value is present in the biological information image, and performs a notification regarding the reference value in a case where it is determined the reference value is not appropriate.

It is preferable that the image processor generates reference value color correspondence information in which a region where the biological information is equal to or lower than the reference value is associated with a specific color, and generates the biological information image on the basis of the reference value color correspondence information.

In addition, it is preferable that in a case where the reference value is set, the image processor generates reference value color correspondence information on the basis of the set reference value.

It is preferable that the image processor generates the display image by using a reference value color bar obtained by forming the reference value color correspondence information as an image, and a reference value index indicating the reference value.

It is preferable that in a case where the reference value is set, the image processor generates the display image by using the reference value index indicating the set reference value.

It is preferable that the image processor calculates an average value of the biological information in the endoscopic image, and generates the display image by using the reference value color bar and an average value index indicating the average value.

It is preferable that the image processor is connected to a display that displays the display image and a display image storage unit that stores the display image, and the image processor performs a control of thumbnail-displaying the display image stored in the display image storage unit on the display.

It is preferable that in a case where the reference value is set, the image processor performs a control of displaying the display image to be thumbnail-displayed on the display after changing the display image on the basis of the reference value.

It is preferable that in a case where the quasi-low value region is present in a preset ratio or more in the biological information image, the image processor determines that the reference value is not appropriate.

It is preferable that in a case where the quasi-low value region continues to be present for a preset time or more the image processor determines that the reference value is not appropriate.

It is preferable that in a case where it is not determined that the reference value is not appropriate, the image processor performs a notification that the reference value is appropriate.

It is preferable that the image processor recognizes a site of the subject on the basis of the endoscopic image, and sets the reference value on the basis of the site.

It is preferable that in a case where the image processor determines that the reference value is not appropriate, the reference value is switched and set to a higher value.

It is preferable that in a case where the reference value and the set value satisfy a preset condition, the image processor changes and sets the reference value to a preset value that is higher than the reference value before a change and does not exceed the set value.

It is preferable that the biological information is an oxygen saturation of the subject.

Additionally, the present invention is a method of operating an image processing device comprising an image processor. The image processor acquires an endoscopic image obtained by imaging a subject with an endoscope, calculates biological information on the basis of the endoscopic image, sets a reference value of the biological information, generates a biological information image obtained by forming the biological information as an image so that a low value region equal to or lower than the reference value and the other region are distinguishable from each other, generates a display image in which the biological information image is superimposed on the endoscopic image, determines that the reference value is not appropriate in a case where a quasi-low value region in which the biological information is higher than the reference value and equal to or lower than a preset set value is present in the biological information image, and performs a notification regarding the reference value in a case where it is determined the reference value is not appropriate.

According to the present invention, overlooking of a portion where the biological information is specific can be prevented.

DESCRIPTION OF THE PREFERRED EMBODIMENTS

Figure 1:
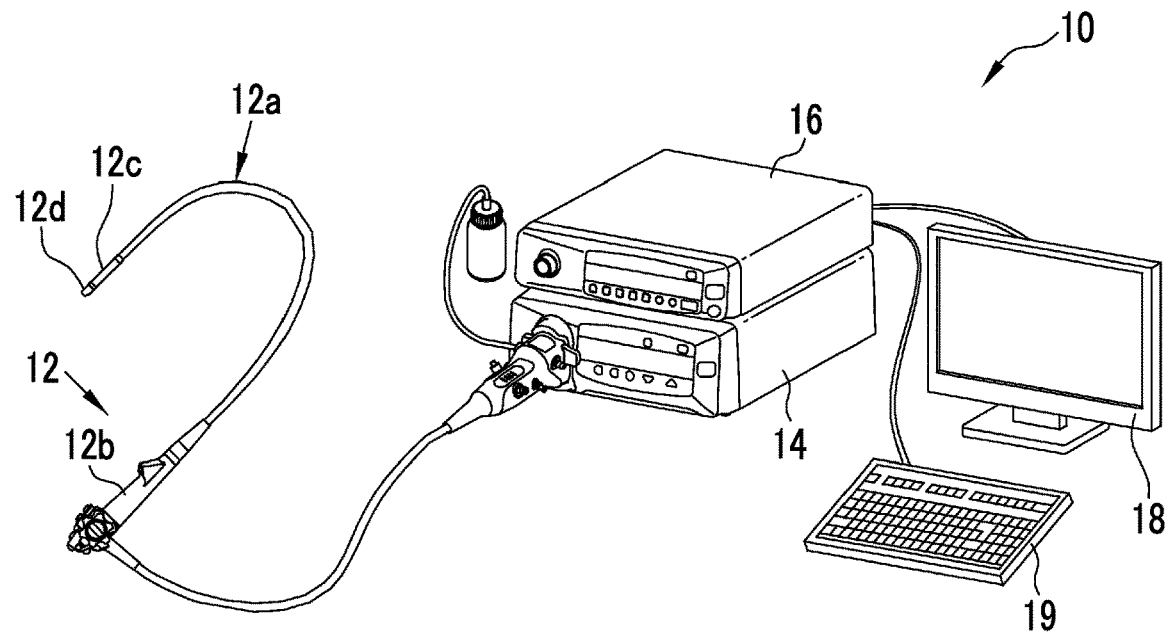
FIG. 1 is an external view of an endoscope system.

As shown in FIG. 1, an endoscope system 10 (endoscope apparatus) comprises an endoscope 12 (scope), a light source device 14, a processor device 16, a display 18, and a keyboard 19. The endoscope 12 images a subject. The light source device 14 generates illumination light. The processor device 16 performs the system control of the endoscope system 10. Additionally, the processor device 16 generates an endoscopic image and performs image processing on the endoscopic image as necessary. That is, the processor device 16 functions as an image processing device. The display 18 is a display unit that displays the endoscopic image or the like. The keyboard 19 is an input device that performs setting input or the like to the processor device 16 and the like.

Figure 2:
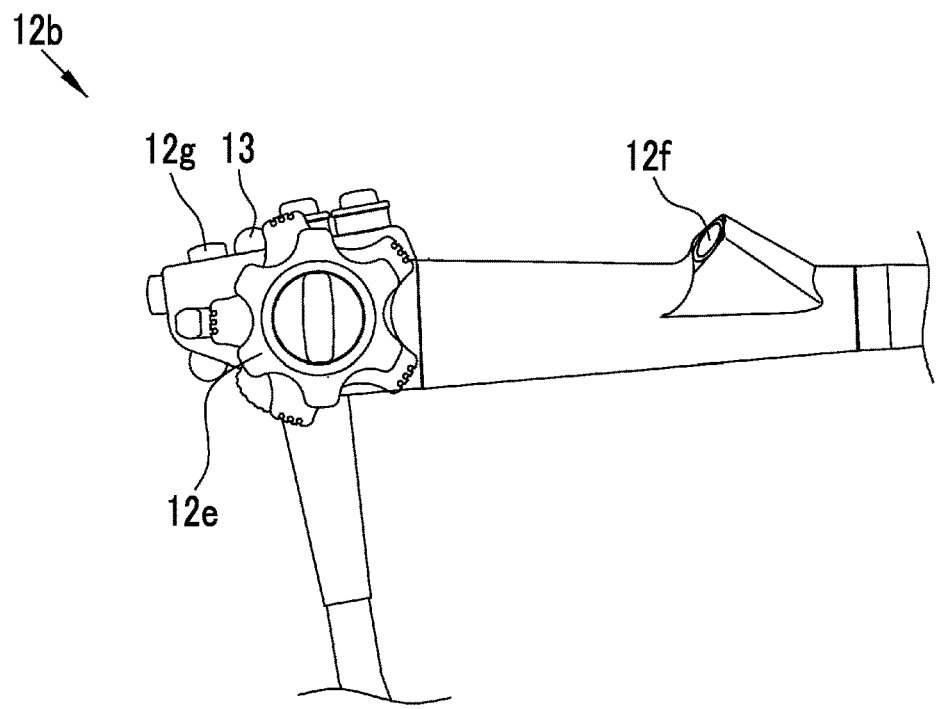
FIG. 2 is an external view of an operating part of an endoscope.

The endoscope 12 has an insertion part 12*a* to be inserted into a subject, an operating part 12*b* provided at a proximal end portion of the insertion part 12*a*, and a bendable part 12*c* provided on a distal end side of the insertion part 12*a*, and a distal end part 12*d*. By operating an angle knob 12*e* (see FIG. 2) of the operating part 12*b*, the bendable part 12*c* is curved. As a result, the distal end part 12*d* faces in a desired direction. Additionally, as shown in FIG. 2, the operating part 12*b* is provided with a treatment tool insertion port 12*f*, a scope button 12*g*, and a zoom operation part 13 in addition to the angle knob 12*e*. The treatment tool insertion port 12*f* is a port that allows a treatment tool such as biopsy forceps, a snare, or an electric scalpel to be inserted thereinto. The treatment tool inserted into the treatment tool insertion port 12*f* protrudes from the distal end part 12*d*. Various operations can be assigned to the scope button 12*g*, and in the present embodiment, the various operations are used for the operation of setting a reference value. By operating the zoom operation part 13, the subject can be enlarged or reduced for imaging.

Figure 3:
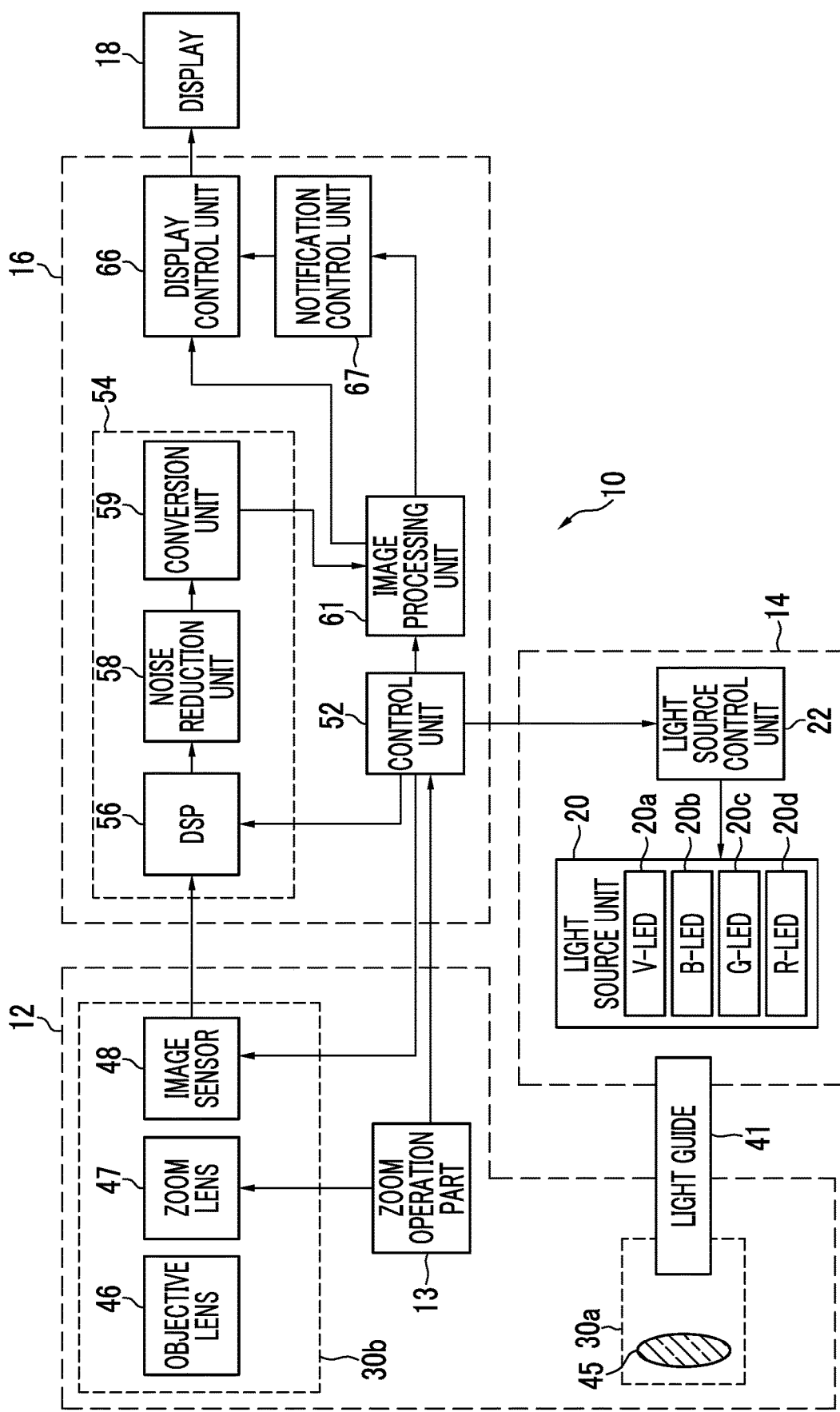
FIG. 3 is a block diagram of the endoscope system.

As shown in FIG. 3, the light source device 14 includes a light source unit 20 that emits illumination light and a light source control unit 22 that controls the operation of the light source unit 20.

The light source unit 20 emits the illumination light with which the subject is illuminated. The emission of the illumination light includes emission of excitation light or the like used for emitting the illumination light. The light source unit 20 includes, for example, a light source of a laser diode, a light emitting diode (LED), a xenon lamp, or a halogen lamp, and generates at least white illumination light or excitation light used to emit the white illumination light. The white includes so-called pseudo-white, which is substantially equivalent to white in imaging the subject using the endoscope 12. The light source unit 20 includes, as necessary, a phosphor that emits light in a case where irradiated with excitation light, an optical filter that adjusts the wavelength range, optical spectrum, light amount, or the like of the illumination light or excitation light, or the like. In addition, the light source unit 20 can emit light having a specific wavelength range necessary for capturing an image used for calculating biological information such as oxygen saturation of hemoglobin contained in the subject.

In the present embodiment, the light source unit 20 has four-color LEDs of a V-LED 20*a*, a B-LED 20*b*, a G-LED 20*c*, and an R-LED 20*d*. The V-LED 20*a* emits violet light VL having a central wavelength of 405 nm and a wavelength range of 380 to 420 nm. The B-LED 20*b* emits blue light BL having a central wavelength of 460 nm and a wavelength range of 420 to 500 nm. The G-LED 20*c* emits green light GL having a wavelength range of 480 to 600 nm. The R-LED 20*d* emits red light RL having a central wavelength of 620 to 630 nm and a wavelength range of 600 to 650 nm. In addition, the central wavelengths of the V-LED 20*a* and the B-LED 20*b* have a width of about ±20 nm, preferably about ±5 nm to about ±10 nm.

The light source control unit 22 controls timings at which each light source constituting the light source unit 20 is turned on or off, or shielded, the amount of light emitted, and the like. As a result, the light source unit 20 can emit a plurality of types of illumination light having different optical spectra. In the present embodiment, the light source control unit 22 makes turn-on and turn-off the LEDs 20*a* to 20*d*, the amount of light emitted during turn-on, the insertion/removal of the optical filter, and the like independent from each other. The optical spectrum of the illumination light is adjusted by inputting a control signal. Accordingly, the light source unit 20 emits white light. Additionally, the light source unit 20 can emit illumination light consisting of at least narrow band light (hereinafter referred to as narrow band light). The "narrow band" means a substantially single wavelength range in relation with the characteristics of the subject and/or the spectral characteristics of the color filter of the image sensor 48. For example, in a case where the wavelength range is, for example, about ±20 nm or less (preferably about ±10 nm or less), this light is the narrow band. Additionally, the wide band means having a relatively wide wavelength range as compared to the narrow band light in relation with the characteristics of the subject and/or the spectral characteristics of the color filter of the image sensor 48. Therefore, in a case where the wavelength range is, for example, ±20 nm or more, the light is the wide band light.

An illumination optical system 30*a* and an imaging optical system 30*b* are provided at the distal end part 12*d* of the endoscope 12. The illumination optical system 30*a* has an illumination lens 45, and the illumination light is emitted toward the subject via the illumination lens 45.

The imaging optical system 30*b* has an objective lens 46, a zoom lens 47, and an image sensor 48. The image sensor 48 images the subject by using reflected light (including scattered light, fluorescence emitted by the subject, or fluorescence caused by drugs administered to the subject, or the light in addition to the reflected light) of the illumination light returning from the subject via the objective lens 46 and the zoom lens 47. The zoom lens 47 moves by operating the zoom operation part 13 to enlarge or reduce the subject image.

The image sensor 48 has one color filter of a plurality of color filters for each pixel. In the present embodiment, the image sensor 48 is a color sensor having a primary color filter. Specifically, the image sensor 48 has an R pixel having a red color filter (R filter), a G pixel having a green color filter (G filter), and a B pixel having a blue color filter (B filter).

In addition, as the image sensor 48, a charge coupled device (CCD) sensor or a complementary metal oxide semiconductor (CMOS) sensor is available. Additionally, although the image sensor 48 of the present embodiment is a primary color sensor, a complementary color sensor can also be used. The complementary color sensors include, for example, a cyan pixel provided with a cyan color filter, a magenta pixel provided with a magenta color filter, a yellow pixel provided with a yellow color filter, and a green pixel provided with a green color filter. In a case where the complementary color sensor is used, an image obtained from a pixel for each of the above colors can be converted into an image similar to an image obtained by the primary color sensor by performing complementary color-primary color conversion. The same applies to a case where the primary or complementary color sensor has one or a plurality of types of pixels having characteristics other than the above, such as W pixels (white pixels that receive light in a nearly full wavelength range). Additionally, although the image sensor 48 of the present embodiment is a color sensor, a monochrome sensor having no color filter may be used.

In the processor device 16, a program (not shown) related to processing or the like performed by a control unit 52, an image acquisition unit 54, an image processing unit 61, a display control unit 66, a notification control unit 67, and the like, which will be described below, is incorporated in a memory. As the program is operated by the control unit 52 constituted by a processor (image processor) included in the processor device 16 which is the image processing device, the functions of the control unit 52, the image acquisition unit 54, the image processing unit 61, and the display control unit 66, the notification control unit 67 are realized.

The control unit 52 performs integrated control of the endoscope system 10 such as synchronous control of the irradiation timing of the illumination light and imaging timing. In a case where various settings are input using the keyboard 19 or the like, the control unit 52 sets the settings in each part of the endoscope system 10 such as the light source control unit 22, the image sensor 48, or the image processing unit 61.

The image acquisition unit 54 acquires the endoscopic image obtained by imaging the subject with the endoscope. More specifically, the image acquisition unit 54 acquires the image obtained by imaging the subject using the pixel for each color, that is, a RAW image, from the image sensor 48. Additionally, the RAW image is an image (endoscopic image) before demosaicing processing is carried out. As long as the image before the demosaicing processing is carried out is used, the RAW image also includes an image obtained by performing optional processing such as noise reduction processing on the image acquired from the image sensor 48.

The image acquisition unit 54 includes a digital signal processor (DSP) 56, a noise reduction unit 58, and a conversion unit 59 in order to perform various processing on the acquired RAW image as necessary to generate the endoscopic image.

The DSP 56 includes, for example, an offset processing unit, a defect correction processing unit, a demosaicing processing unit, a linear matrix processing unit, a YC conversion processing unit, and the like (none of which are shown). The DSP 56 performs various processing on the RAW image or an image generated by using the RAW image by using these units.

The offset processing unit performs offset processing on the RAW image. The offset processing is the processing of reducing a dark current component from the RAW image and setting an accurate zero level. The offset processing may be referred to as clamp processing. The defect correction processing unit performs defect correction processing on the RAW image. In a case where the image sensor 48 includes a pixel having a defect (defective pixel) caused by a manufacturing process or a change with time, the defect correction processing is the processing of correcting or generating a pixel value of a RAW pixel corresponding to the defective pixel of the image sensor 48. The demosaicing processing unit performs the demosaicing processing on a RAW image for each color corresponding to a color filter for each color. The demosaicing processing is the processing of generating a pixel value, which is missing due to the arrangement of color filters in the RAW image, by interpolation. The linear matrix processing unit performs linear matrix processing on the endoscopic image generated by assigning one or a plurality of RAW images to a channel for each RGB color. The linear matrix processing is the processing of enhancing the color reproducibility of the endoscopic image. The YC conversion processing performed by the YC conversion processing unit is the processing of converting the endoscopic image, which is generated by assigning one or a plurality of RAW images to the channel for each RGB color, into an endoscopic image having a brightness channel Y, a color difference channel Cb, and a color difference channel Cr.

The noise reduction unit 58 performs the noise reduction processing on the endoscopic image having the brightness channel Y, the color difference channel Cb, and the color difference channel Cr by using, for example, a moving average method or a median filter method. The conversion unit 59 reconverts the brightness channel Y, the color difference channel Cb, and the color difference channel Cr after the noise reduction processing into the endoscopic image having the channel for each BGR color.

Figure 4:
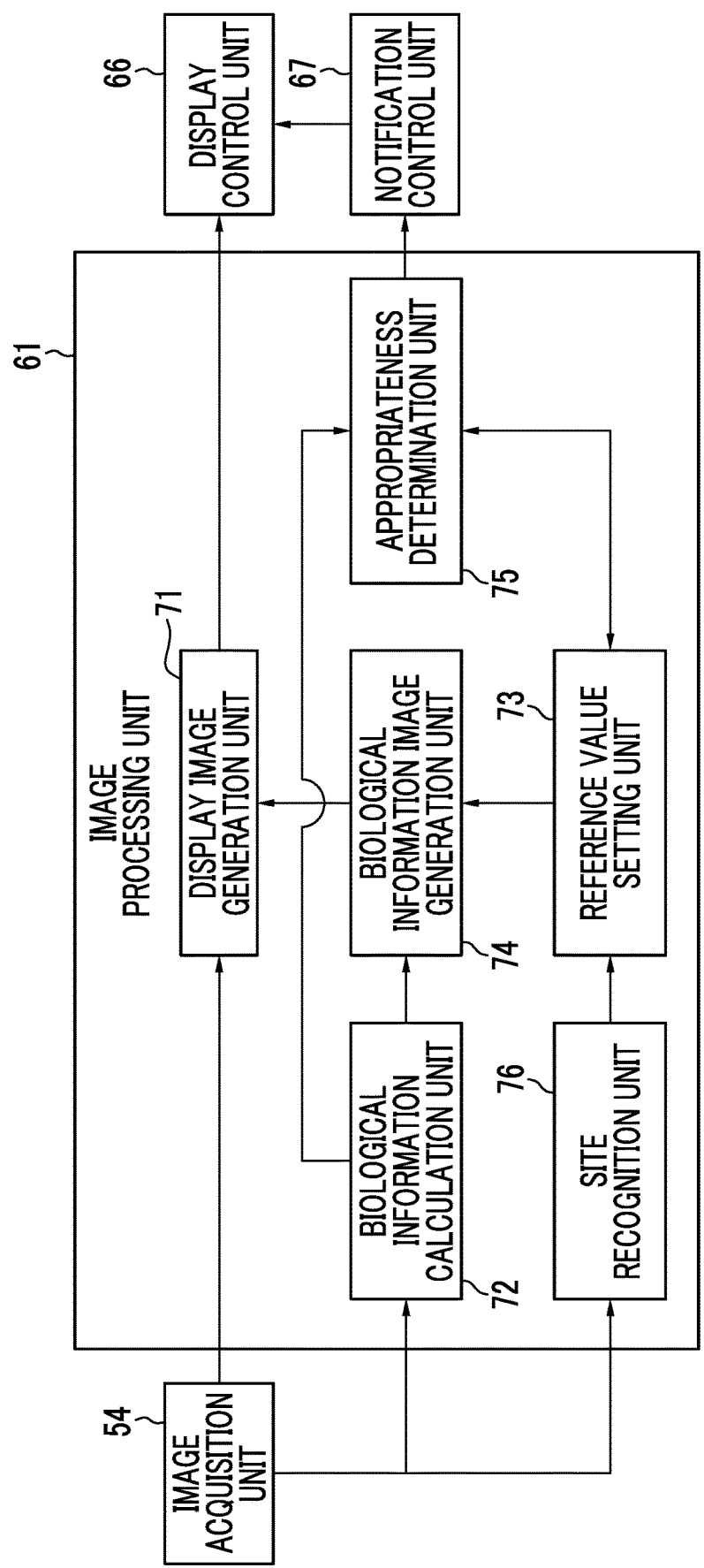
FIG. 4 is a block diagram of an image processing unit.

The image processing unit 61 performs necessary image processing on the endoscopic image output by the image acquisition unit 54. Additionally, the image processing unit 61 performs calculations using the endoscopic image output by the image acquisition unit 54. Specifically, as shown in FIG. 4, the image processing unit 61 comprises a display image generation unit 71, a biological information calculation unit 72, a reference value setting unit 73, a biological information image generation unit 74, an appropriateness determination unit 75, a site recognition unit 76, and the like.

The display image generation unit 71 acquires the endoscopic image from the image acquisition unit 54 and generates an endoscopic image (hereinafter, referred to as a display image) to be used for display on the display 18 or the like. For example, the display image generation unit 71 acquires a B image obtained by imaging the subject using the B pixel, a G image obtained by imaging the subject using the G pixel, and an R image obtained by imaging the subject using the R pixel from the image acquisition unit 54, and generates the display image by using all or some of these images. Additionally, the generation of the display image performed by the display image generation unit 71 includes performing and outputting necessary image processing on one endoscopic image acquired from the image acquisition unit 54, and outputting one endoscopic image acquired from the image acquisition unit 54 as it is, in addition to using a plurality of endoscopic images to obtaining the endoscopic image different from the plurality of images.

Additionally, the display image generation unit 71 performs necessary image processing on the endoscopic image acquired from the image acquisition unit 54 in a case where the display image is generated. The image processing performed by the display image generation unit 71 is, for example, enhancement processing for enhancing the subject or a part of the subject. The enhancement means making it possible to obtain information on a specific portion by distinguishing the specific portion from other tissues or structures. For example, the processing of enclosing a portion having a specific feature with a frame to show the contour, or changing the color or brightness relative to another portion (for example, normal mucous membrane) is the enhancement processing.

Additionally, the display image generation unit 71 acquires a biological information image from the biological information image generation unit 74 and generates a display image in which the biological information image is superimposed on the endoscopic image. Therefore, the image processing performed by the display image generation unit 71 is, for example, the superimposition processing of generating the display image in which the biological information image generated by the biological information image generation unit 74 is superimposed on the endoscopic image. Moreover, the display image generation unit 71 generates a display image using a color bar, a reference value index, an average value index, or the like. The color bar is an image obtained by forming, as an image, color correspondence information used in a case where the biological information image is generated. Additionally, the reference value index indicates a reference value in the color bar. In addition, the average value index indicates the average value of the biological information in the endoscopic image in the color bar. The generation of the biological information image and the like will be described below.

In addition, the "superimposing" the biological information image on the endoscopic image means that, at least in a case where the display image or the like is displayed on the display 18 or the like, the biological information image is overlappingly displayed on the display image, or the like in an aspect in which the display image can be distinguished and recognized from the subject reflected in the display image or the like, and includes synthesizing (integrating) the biological information image with the display image or the like in addition to overlappingly displaying the biological information image on the display image or the like in a separable manner. In the present embodiment, the display image generation unit 71 superimposes the biological information image on the display image or the like in a separable manner.

The biological information calculation unit 72 calculates the biological information related to the subject on the basis of the endoscopic image acquired from the image acquisition unit 54. The biological information is a numerical value or the like representing the whole or partial characteristics of the subject, for example, oxygen saturation, blood concentration, blood vessel density, probability having a specific form such as lesions or lesion candidates (including targets for biological tissue examination), or the like.

In the present embodiment, the biological information calculation unit 72 calculates the oxygen saturation of the subject for each pixel, using the endoscopic image acquired from the image acquisition unit 54. For the calculation of the oxygen saturation, for example, the calculation can be performed using a B image obtained by imaging the subject using a narrow band light having a wavelength of about 470 nm, a G image obtained by imaging using a wide band green light, and an R image obtained by imaging the subject using a wide band red light. More specifically, the ratio of the B image to the G image (hereinafter referred to as B/G) and the ratio of the R image to the G image (hereinafter referred to as R/G) are obtained for each pixel. In addition, a table or the like for associating B/G and R/G with the value of the oxygen saturation by experiments or simulations is prepared in advance. Then, the oxygen saturation is calculated using the above table from the calculated values of B/G and R/G. In addition, in a case where the biological information calculation unit 72 calculates the oxygen saturation, the image acquisition unit 54 acquires each of these images and provides the acquired image to the biological information calculation unit 72.

The reference value setting unit 73 sets a reference value for the biological information. The reference value is a threshold value for distinguishing a region having the biological information equal to or lower than this value from a region other than this value. By setting the reference value, reference value color correspondence information is generated. By using the biological information calculated by the biological information calculation unit 72 and the reference value color correspondence information, the biological information image obtained by forming the biological information as an image is generated.

The units that set the reference value may be any units as long as the value of the reference value can be specified. The reference value may be optionally specified by a user or may be automatically specified depending on conditions or the like. In the present embodiment, since the reference value is the reference value of the oxygen saturation, specifically, the reference value is specified so as to be an optional value within a range of 0% or more and 100% or less. For example, the reference value is optionally specified in 1% increments within this range.

Specifically, the units for the user to optionally specify the reference value can be set, for example, by inputting a numerical key using a keyboard 19 or the like. Additionally, similarly, the units may be set by raising or lowering the numerical value with arrow keys on the keyboard 19. Additionally, the units may be set by raising or lowering the numerical value through the operation of the scope button 12g or a foot switch (not shown) of the endoscope. In that case, the scope button 12g or the like may be changed by 1% each time the scope button is pressed once and may be changed continuously by pressing and holding the scope button for a long time.

In addition, a site recognition unit 76 (see FIG. 4) that recognizes a site of the subject on the basis of the endoscopic image may be provided. Then, the reference value setting unit 73 may set the reference value on the basis of the site recognized by the site recognition unit 76. For example, in a case where the biological information is the oxygen saturation, the average value or the like of the oxygen saturation may differ depending on the site. In that case, it is not necessary to manually reset the reference value, and the reference value can be simply changed and set, which is preferable.

The site recognition unit 76 recognizes a site on the basis of the endoscopic image. The site to be recognized is, for example, the type of organs such as the esophagus, stomach, or duodenum in a case in where the upper gastrointestinal tract is imaged. Additionally, the type of sites such as the cardia, fundus, gastric corpus, large bay, vestibule, pylorus, duodenum, or small bay is recognized within the same organ, for example, in the stomach. As the recognition method, a method by the image processing can be used, and an image recognition method using a learned model by machine learning may be used.

Figure 5:
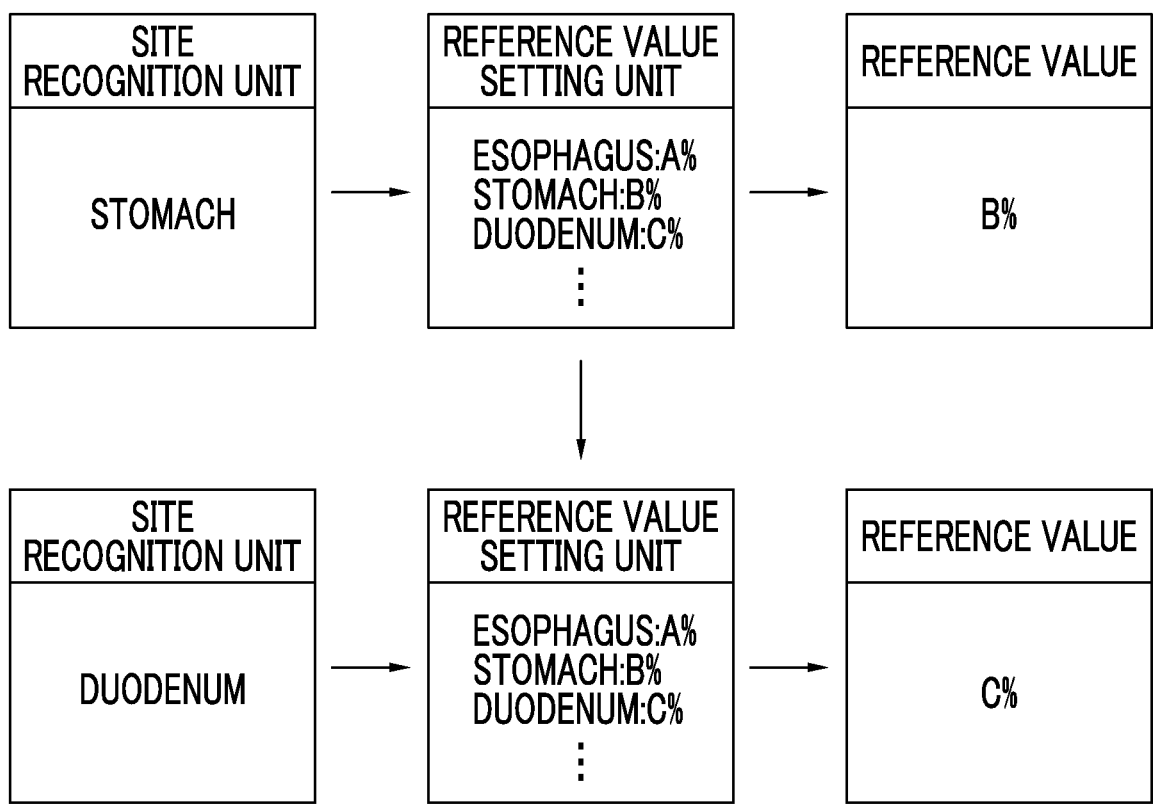
FIG. 5 is an explanatory view illustrating a reference value set by a reference value setting unit on the basis of a site.

As shown in FIG. 5, for example, in an examination by the endoscope, in a case where the site recognition unit 76 recognizes that the site is the stomach on the basis of the endoscopic image, the reference value setting unit 73 sets the reference value to B % in accordance with correspondence information in which the site and the reference value correspond to each other. The reference value setting unit 73 comprises this correspondence information in advance. Then, in a case where the examination progresses and the site recognition unit 76 recognizes that the site is the duodenum on the basis of the endoscopic image, the reference value setting unit 73 sets the reference value to C % in accordance with the reference value set for each site. By setting the reference value on the basis of the type of the site recognized by the site recognition unit 76, it is preferable because an appropriate reference value can be simply set even in a case where the level of the biological information differs depending on the site.

The biological information image generation unit 74 generates a biological information image formed as an image so that a region in which the biological information is equal to or lower than the reference value (hereinafter referred to as a low value region) and a region in which the biological information is higher than the reference value are distinguishable from each other. As a method for forming the biological information as an image so as to be distinguishable between the low value region and the other region, any method may be used as long as the low value region and a region higher than the low value region can be formed as an image so as to be distinguishable from each other. For example, there is a method of displaying different colors, patterns, or shapes in the low value region and the other region on the basis of the biological information calculated for each pixel of the endoscopic image, or a method of displaying colors or the like only in the low value region and not displaying the color or the like in the other region.

As the method of generating the biological information image obtained by forming the biological information as an image so that the low value region and the region higher than the reference value are distinguishable, it is preferable that the biological information image generation unit 74 generates the reference value color correspondence information in which the biological information equal to or lower than the reference value is associated with a specific color, and generates the biological information image on the basis of the reference value color correspondence information. The reference value color correspondence information is color correspondence information in which a specific color, for example, blue is associated with the biological information equal to or lower than the reference value. Accordingly, blue is displayed on the basis of the reference value color correspondence information in a pixel portion where the biological information is equal to or lower than the reference value, and no color is displayed in the region higher than the reference value. Therefore, in the generated biological information image, the low value region is displayed in blue, and the region higher than the reference value is a colorless image. Therefore, the low value region and the other region are distinguishable from each other.

In addition, the specific color includes colorless or transparent. In the present embodiment, the biological information image generation unit 74 generates a biological information image to which a color corresponding to the measured value of the oxygen saturation for each pixel is applied, depending on the measured value of the oxygen saturation calculated for each pixel in the endoscopic image and the reference value color correspondence information. Therefore, a biological information image in which an absolute value such as the measured value of the oxygen saturation and the color correspond to each other is generated.

Additionally, the reference value color correspondence information may be one in which the biological information equal to or higher than a preset value and a specific color different from that in a case where the biological information is equal to or lower than the reference value are associated with each other in addition to associating the biological information equal to or lower than the reference value with the specific color. In the present embodiment, since the biological information is the oxygen saturation, the oxygen saturation is sufficiently high, and for example, an oxygen saturation of 95% or more is associated with, for example, red. In this case, the reference value color correspondence information is correspondence information in which the low value region of the oxygen saturation is colored in blue, a region higher than the reference value and lower than 95% is colored colorlessly, and a region (hereinafter referred to as a high value region) of 95% or more is colored in red.

The generated biological information image is sent to the display image generation unit 71. The display image generation unit 71 performs the superimposition processing of generating the display image in which the biological information image is superimposed on the endoscopic image. The superimposition processing may include the processing necessary for superimposing the endoscopic image and the biological information image on each other. For example, the superimposition processing may include processing such as the alignment between the endoscopic image and the biological information image and light amount ratio correction of each image.

Figure 6:
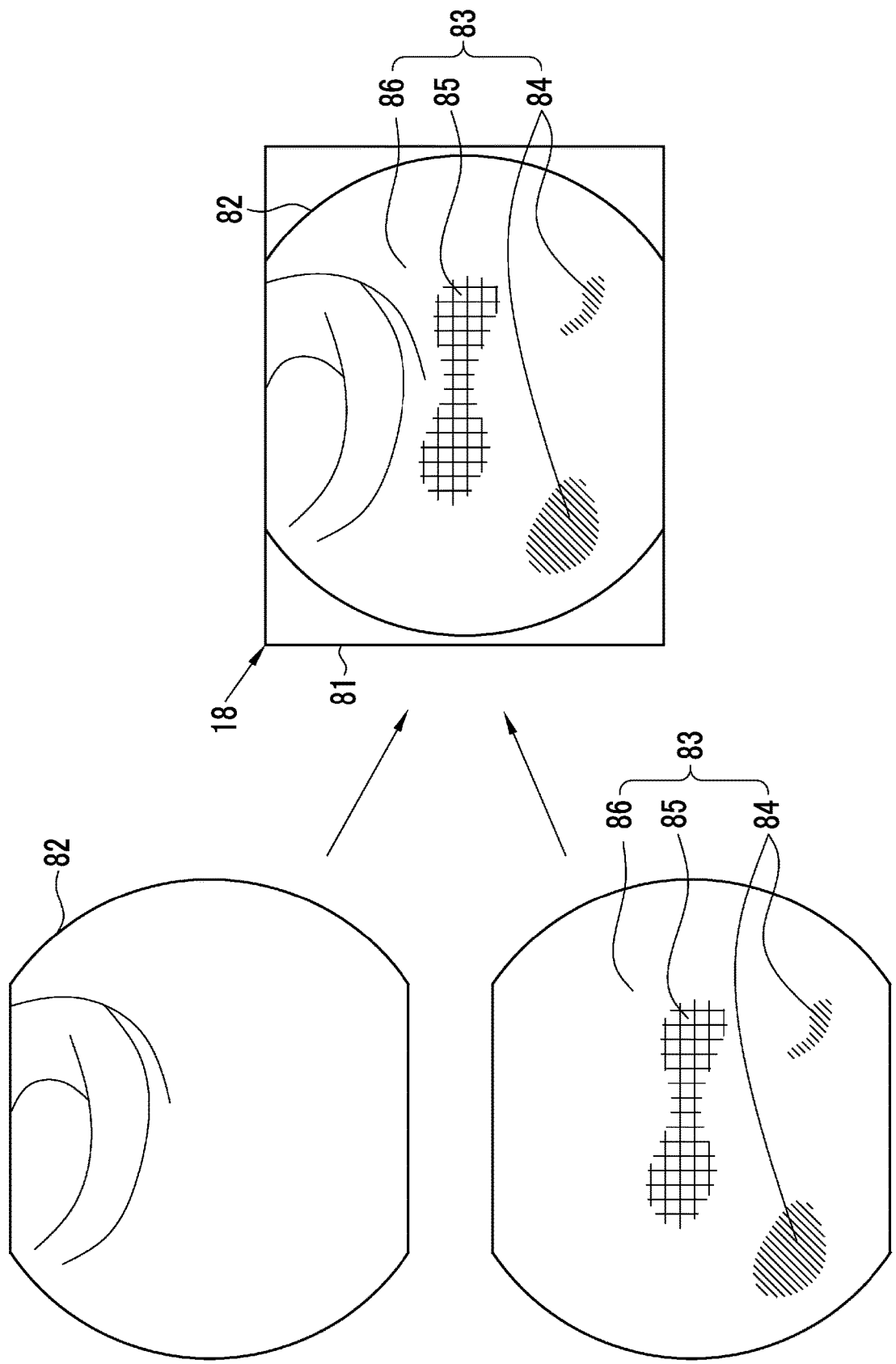
FIG. 6 is an explanatory view illustrating the generation of a display image.

As shown in FIG. 6, the display image generation unit 71 specifically superimposes the endoscopic image 82 and the oxygen saturation image (biological information image) 83 on each other to generate a display image 81 in the present embodiment. In the oxygen saturation image 83, a low value region 84 of the oxygen saturation is colored in a specific color and formed as an image so that the low value region 84 of the oxygen saturation and a region having a higher oxygen saturation than the reference value are distinguishable from each other. Therefore, in the oxygen saturation image 83, the low value region 84 is colored and shown in, for example, blue. An intermediate region 86 having a higher oxygen saturation than the reference value and lower than 95%, is colorless, and a high value region 85 is colored in, for example, red. In the display image 81 superimposed on the endoscopic image 82, the low value region 84 is displayed in blue, the high value region 85 is displayed in red, and the intermediate region 86 is displayed as the endoscopic image 82 remains, for example, in the natural color of the subject. In addition, in FIG. 6, the low value region 84 is shown by diagonal lines, the high value region 85 is shaded, and the intermediate region 86 is shown blank. The display image 81, which is an image obtained by superimposing the endoscopic image 82 and the oxygen saturation image (biological information image) 83 on each other, is displayed on the display 18.

Figure 7:
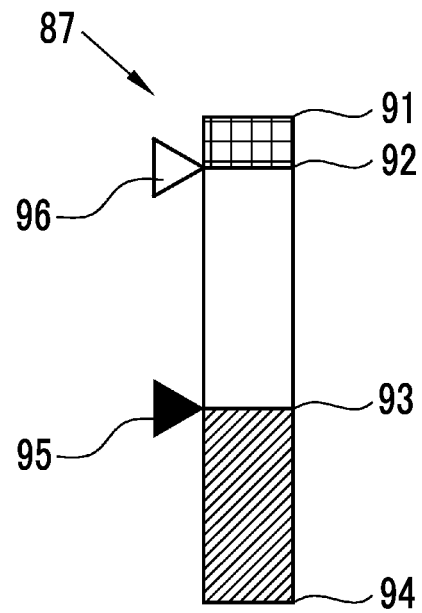
FIG. 7 is a reference value color bar.

It is preferable that the biological information image generation unit 74 generates a reference value color bar obtained by forming the reference value color correspondence information as an image. As shown in FIG. 7, for example, the reference value color bar 87 is an image obtained by forming the measured value color correspondence information as an image. Since the reference value color bar 87 is a color bar for the reference value of the oxygen saturation, a scale 91 indicates an oxygen saturation of 100%, a scale 93 indicates an oxygen saturation of 40%, and a scale 94 indicates an oxygen saturation of 0%. Additionally, a scale 92 is a high value region 85 and indicates an oxygen saturation of 95%. In addition, a reference value index 95 indicating the reference value is attached to the scale 93 in the shape of a filled triangular arrow, for example, and a high value index 96 is attached to the scale 92 indicating the high value region 85 in the shape of, for example, a white triangular arrow. The display image 81 including the reference value color bar 87 allows the user to identify the level of the oxygen saturation to be colored on the basis of the biological information image 83, at a glance.

The display image generation unit 71 may generate the display image by using the reference value color bar 87. Additionally, it is preferable that the display image generation unit 71 generates the display image 81 by using the reference value color bar 87 and the reference value index 95. The reference value index 95 may be any as long as the reference value can be recognized by the user. Therefore, the reference value index 95 is, for example, in the shape of an arrow or a line. A combination of the reference value color bar 87 and the reference value index 95 is close to an image (hereinafter referred to as a superimposed image) in which the endoscopic image 82 and the biological information image 83 are superimposed each other, and is preferably displayed at a point where there is no problem in visually recognizing the superimposed image. By displaying the combination close to the superimposed image, the color and the reference value is easily recognized in the biological information image in the superimposed image.

Figure 8:
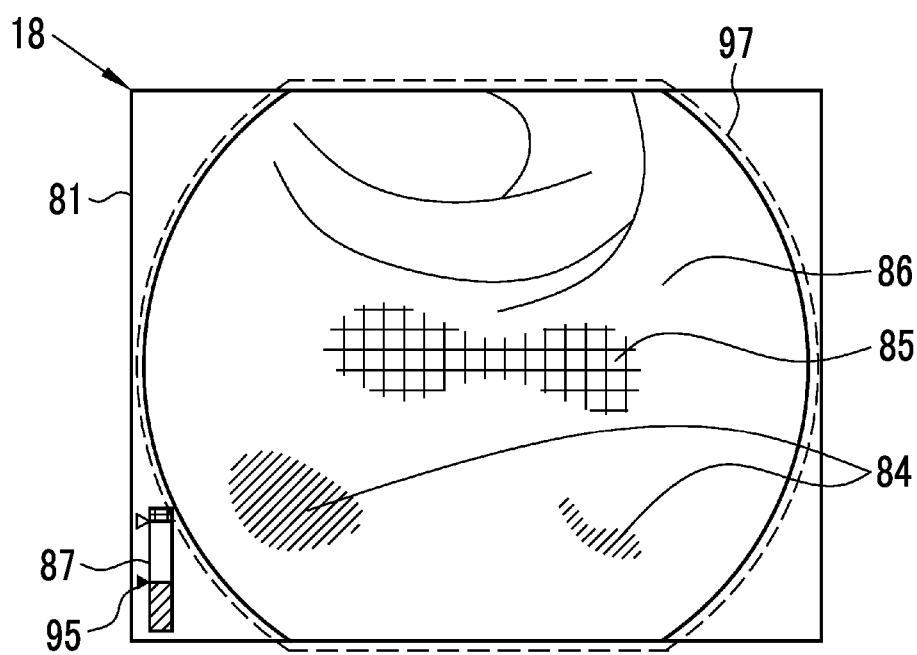
FIG. 8 is an image diagram of the display image including the reference value color bar.

Specifically, as shown in FIG. 8, for example, the display image 81 is generated by disposing the reference value color bar 87 to which the reference value index 95 is attached on the lower left of the superimposed image 97 on the screen of the display. By displaying the reference value color bar 87 to which the reference value index 95 is attached, the user can recognize at a glance how much the current reference value is.

In addition, it is preferable that in a case where the reference value setting unit 73 sets the reference value, the biological information image generation unit 74 generates the reference value color correspondence information on the basis of the set reference value. That is, each time the reference value setting unit 73 sets the reference value, the reference value color correspondence information may be generated. The reference value setting unit 73 changes the reference value depending on an instruction or the like from the user. In a case where the reference value is changed, the biological information image generation unit 74 automatically changes the reference value color correspondence information and generates the biological information image on the basis of the changed reference value color correspondence information.

Additionally, it is preferable that in a case where the reference value setting unit 73 sets the reference value, the display image generation unit 71 generates the display image by using the reference value index 95 indicating the set reference value. The reference value setting unit 73 changes the reference value depending on an instruction or the like from the user. The biological information image generation unit 74 generates the reference value color correspondence information on the basis of the set reference value and generates the reference value color bar 87 on the basis of the reference value color correspondence information. The display image generation unit 71 generates the display image 81 including the generated reference value color bar 87.

Figure 9:
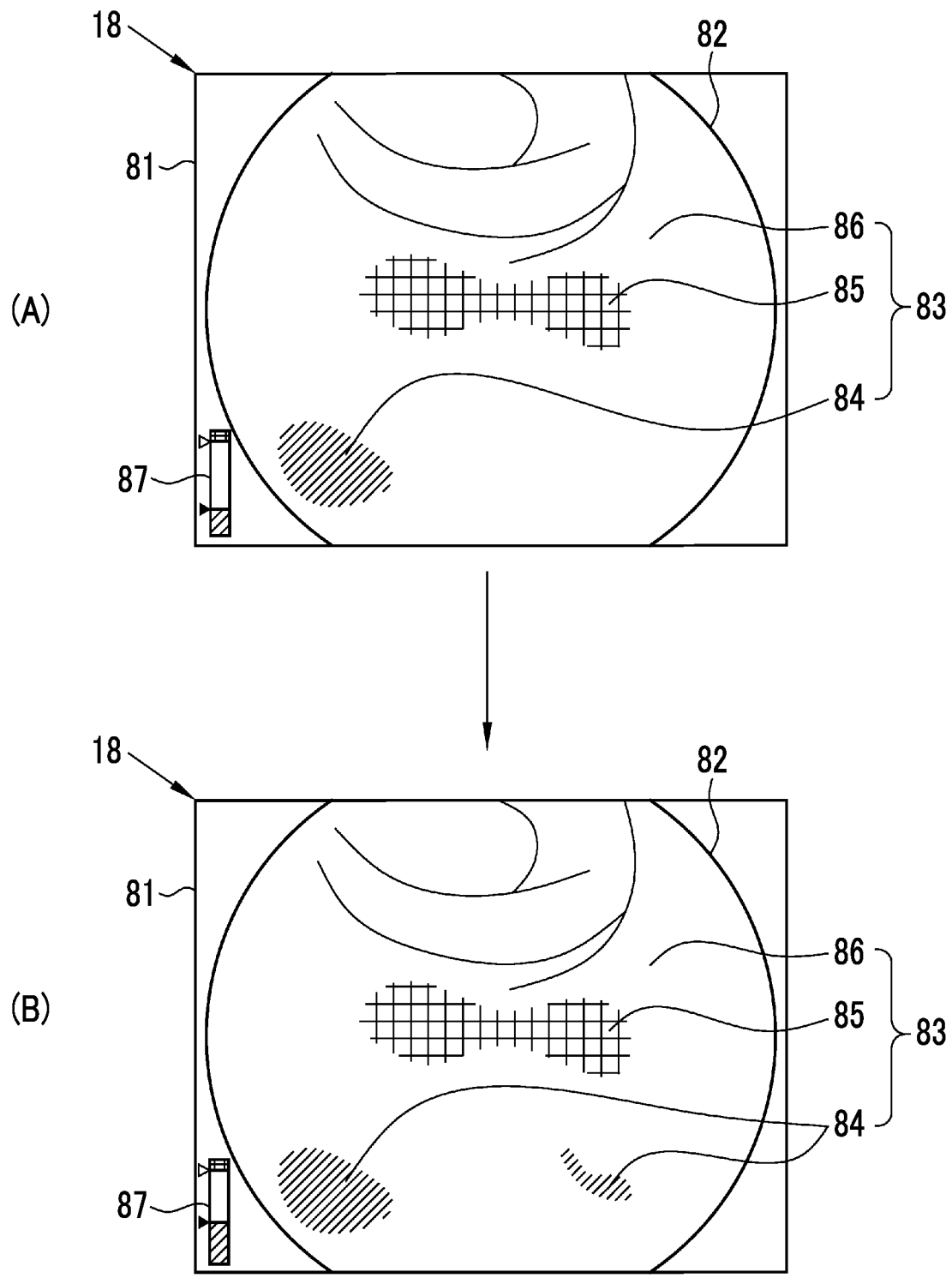
FIG. 9 is an explanatory view illustrating a change in the reference value and the display image.

As shown in (A) of FIG. 9, for example, the reference value setting unit 73 sets the reference value to a value having a higher oxygen saturation, which is the biological information, again with respect to the reference value of 30% of the oxygen saturation before the reference value is changed. As shown in (B) of FIG. 9, by setting the reference value again, the biological information image is changed, and in a case where there is a region equal to or lower than the reference value, the biological information image is displayed. In (B) of FIG. 9, since the reference value is set to 40%, a region in a range where the oxygen saturation is higher than 30% and equal to or lower than 40%, which has not been displayed before the reference value is changed, is displayed. Additionally, each time the reference value is set, the reference value color bar 87 and the reference value index 95 constituting the display image 81 are changed.

Each time the reference value setting unit 73 sets the reference value, the reference value color correspondence information is generated. Accordingly, each time the reference value is set, the biological information image 83 obtained by forming the biological information as an image so that the low value region 84 and the region higher than the reference value are distinguishable from each other, and the reference value color bar 87 obtained by forming the reference value color correspondence information as an image are generated. By generating the biological information image 83 and the reference value color bar 87, the display image 81 using the biological information image 83 or the like is also generated. Additionally, in a case where the reference value setting unit 73 sets the reference value, the display image generation unit 71 generates the display image 81 by using the generated reference value color bar 87 and the reference value index 95 indicating the set reference value. Therefore, in a case where the reference value is changed by the user or automatically, it is possible to automatically and immediately change the display image 81 to one based on the changed reference value. Additionally, in the changed display image 81, it is possible to change and display the reference value color bar 87 to which the reference value index 95 is attached. Each time the reference value is set, the reference value color bar 87 and the reference value index 95 constituting the display image 81 are changed. Therefore, the user can immediately recognize that the reference value has been changed ad how much the reference value after the change is.

In addition, it is preferable that the biological information calculation unit 72 calculates the average value of the biological information in the endoscopic image 82 and the display image generation unit 71 generates the display image 81 by using the average value index indicating the average value. The average value of the biological information in the endoscopic image 82 may be, for example, an average value obtained by adding the biological information calculated on the basis of the endoscopic image 82, or an average value based on a median value. Additionally, the average value may be, for example, a value obtained by performing averaging after portions where the contrast or the like is extremely different in the endoscopic image 82 are excluded. The average value index may be any as long as the average value can be recognized by the user. Therefore, the average value index is, for example, the shape of an arrow or a line, similar to the reference value index 95. However, in a case where both the reference value index 95 and the average value index are displayed, these indexes are distinguishable from each other, for example, by making shapes or colors different from each other. It is preferable that the combination of the reference value color bar 87 and the average value index is displayed close to the superimposed image 97 and at a point where there is no problem in visually recognizing the superimposed image 97. By displaying the combination close to each other, the color and the average value in the biological information image 83 are easily recognized in the superimposed image 97.

Figure 10:
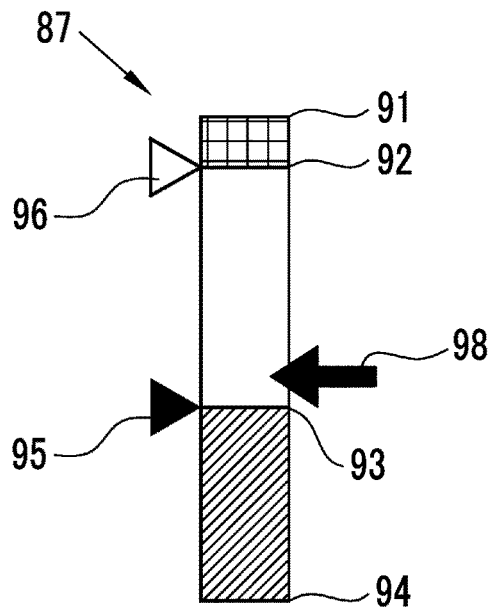
FIG. 10 is a reference value color bar in which an average value index is combined.
Figure 11:
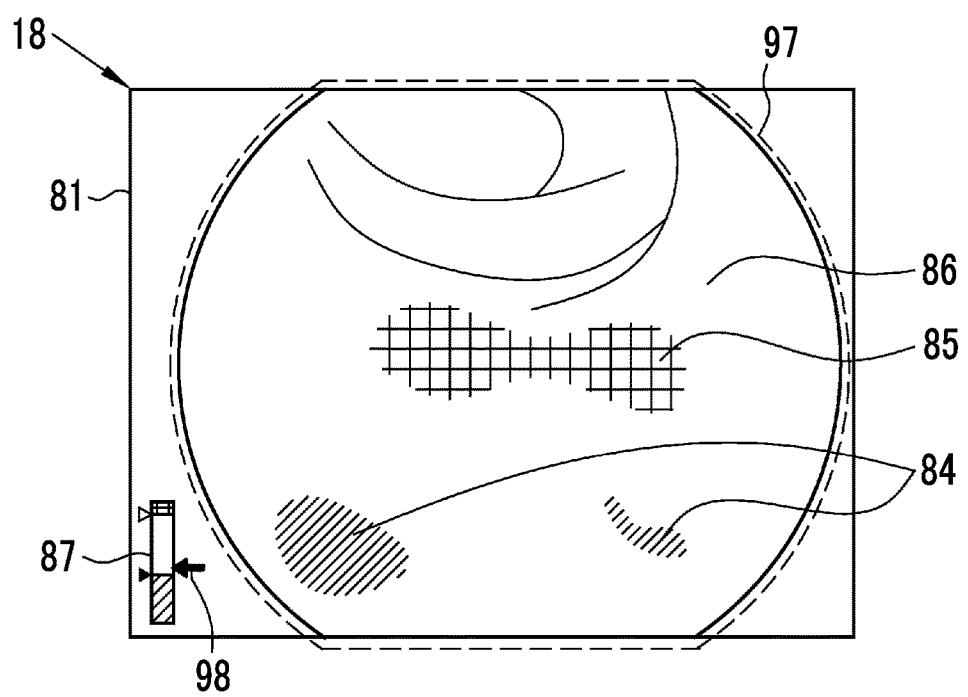
FIG. 11 is an image diagram of a display image including a reference value color bar in which an average value index is combined.

Specifically, as shown in FIG. 10, for example, the reference value color bar 87 and an average value index 98 are combined with each other. As shown in FIG. 11, the display image generation unit 71 generates the display image 81 by disposing one in which the average value index 98 is attached to the reference value color bar 87, on the lower left of the superimposed image 97. By displaying the average value index 98 on the display image 81, the user can immediately recognize how much the current average value is. Additionally, by combining with the reference value index 95, a difference between the average value and the reference value of the biological information in the endoscopic image 82 can be recognized at a glance. For example, in a case where the reference value and the average value are values close to each other, it is expected that a low value region (hereinafter, a quasi-low value region), which is not the low value region 84 but has higher biological information than the reference value and needs interest, is present, and the area thereof is large to some extent. On the other hand, in a case where the reference value and the average value are values distant from each other, it can be expected that the quasi-low value region is not present, or even in a case where the quasi-low value region is present, the area thereof is small.

The appropriateness determination unit 75 determines whether or not the reference value of the biological information is appropriate. In a case where the reference value is appropriate, the low value region 84 is enhanced by the color or the like in the display image 81. Therefore, a region of interest is less likely to be overlooked. This is because the display image 81 includes the biological information image 83 in which biological information equal to or lower than the reference value and the other biological information higher than the reference values are formed as an image so as to be distinguishable between the low value region 84 and the other region.

The case where the reference value is not appropriate includes a case where the reference value is too low. Since the reference value is too low, the low value region 84 is not present on the display image 81 including the biological information image 83, and the biological information image 83 appears to have no region having the value of the biological information of interest. However, in some cases, the quasi-low value region may be provided. The quasi-low value region is a region where the biological information is higher than the reference value but the possibility of a lesion is low to some extent. Therefore, in a case where the reference value is not appropriate, there is a possibility that the quasi-low value region is overlooked. The quasi-low value region is used as a determination material for determining whether or not the reference value is appropriate.

The quasi-low value region is determined depending on a preset set value and the reference value. Since the appropriateness determination unit 75 receives the information of the biological information in the endoscopic image 82 by the biological information calculation unit 72, sets the set value, and also receives the information of the reference value from the reference value setting unit 73, the appropriateness determination unit 74 can determine where or not the quasi-low value region is present.

The set value is set by the appropriateness determination unit 75, and is set in accordance with the site, the purpose of observation, or the like. The set value may be higher than the reference value and may be set in accordance with the value of the reference value, the type and site of the subject of the biological information image 83, the purpose of observation, and the like. For example, in a case where the reference value is set low, the difference between the reference value and the set value is set to be large, and in a case where the reference value is set high, the difference between the reference value and the set value is set to be small. Accordingly, the quasi-low value region can be determined so as not to overlook the quasi-low value region, which is a region of interest. The set reference value and the set value may be displayed on, for example, the display image 81.

Figure 12:
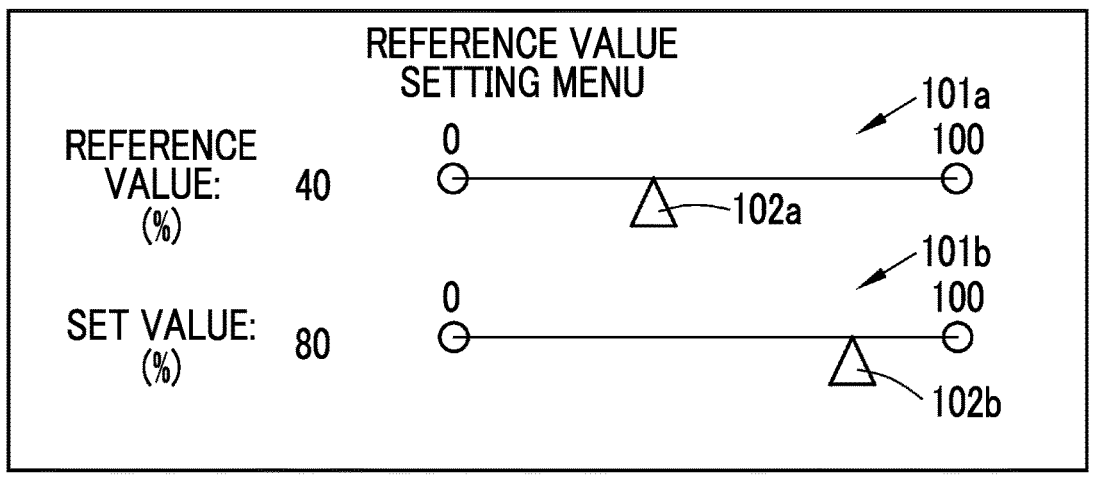
FIG. 12 is an explanatory view of a reference value setting menu.

Additionally, in a case where the reference value and the set value are set, a reference value setting menu may be displayed on the display. Regarding the reference value setting menu, for example, in a case where a reference value setting operation is received by the operation of the keyboard 19, the reference value setting unit displays the reference value setting menu as shown in FIG. 12 on the display 18. The reference value can be changed, for example, from 0% to 100% and is assigned on a slide bar 101*a*. The set value can also be changed, for example, from 0% to 100% and is assigned on a slide bar 101*b*. In a case where the reference value is changed, the reference value is changed by operating the keyboard 19 or the like to align the slider 102*a* with a position on the slide bar 101*a* indicating the reference value to be changed. As for the set value, the set value is also changed by operating the keyboard 19 to align the slider 102*b* with a position on the slide bar 101*b* indicating the set value to be changed. In the present embodiment, an oxygen saturation of 40% is assigned as the reference value by the slide bar 101*a*, and an oxygen saturation of 80% is assigned as the set value by the slide bar 101*b*.

In addition, it is preferable that in a case where the reference value and the set value satisfy the preset conditions, the reference value setting unit 73 changes and sets the reference value to a preset value that is higher than the reference value before the change and does not exceed the set value. This is because in a case where the reference value is too low, by simply switching and setting the reference value to an appropriate value, the reference value can be changed appropriately without any trouble and the low value region 84 can be displayed appropriately.

Additionally, in a case where the quasi-low value region is present, the quasi-low value region can be included in the low value region 84 by switching and setting the reference value to an appropriate value. Therefore, the region that has been the quasi-low value region can be together displayed on the biological information image 83, and by displaying a portion in which the biological information including the region that has been the quasi-low value region and the low value region 84 is specific is displayed to prevent these regions from being overlooked. In addition, the details of the preset conditions and the preset values are appropriately set depending on, for example, the site or the purpose of observation.

Figure 13:
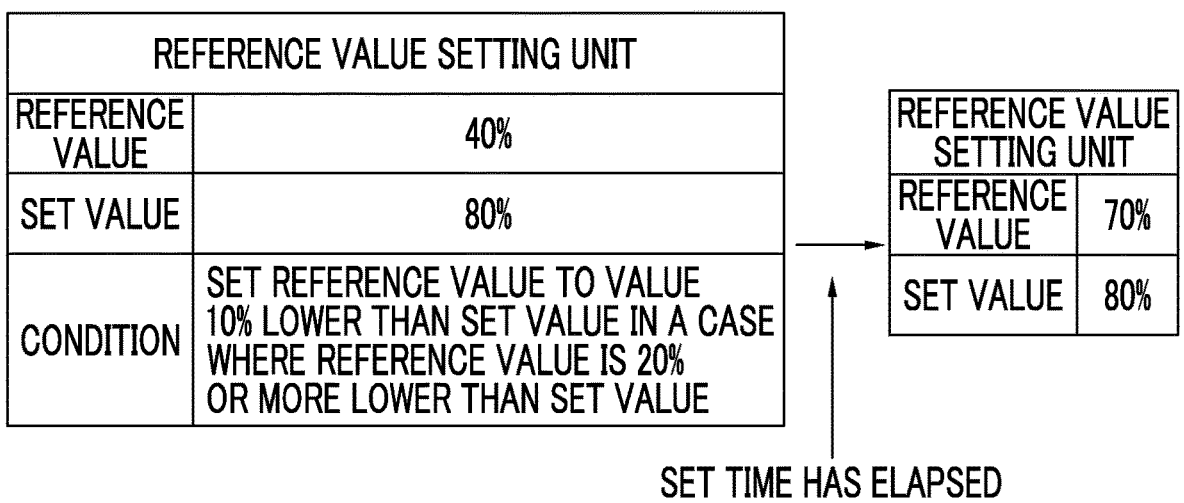
FIG. 13 is an explanatory view illustrating the reference value set by the reference value setting unit on the basis of the reference value and a set value.

Specifically, as shown in FIG. 13, for example, in a case where the reference value is set to 40%, the set value is set to 80%, and detailed observation of a site where there is a possibility of a lesion is performed, and in a case where the preset condition is a case where "the reference value is changed to a value in which the reference value is 10% lower than the set value in a case where the reference value is 20% or more lower than the set value", the condition that the reference value is 30% lower than the set value and the reference value is 20% or more lower than the set value" is satisfied. Therefore, the reference value setting unit 73 switches and sets the reference value to 70%. It is preferable that the switching of the reference value is performed, for example, in a case where a preset time has elapsed, or in a case where the site recognition unit 76 or the like recognizes that the subject has been changed. For example, in a case where a movement is made from a site where detailed observation has been performed by lowering the reference value to another site and the screening of observing where there is a lesion is performed, it is conceivable that the low value region 84 is rarely displayed on the biological information image 83 because the reference value is too low. However, as the reference value setting unit 73 switches and sets the reference value, the low value region 84 can be appropriately displayed even in a case where the site to be observed is moved.

Figure 14:
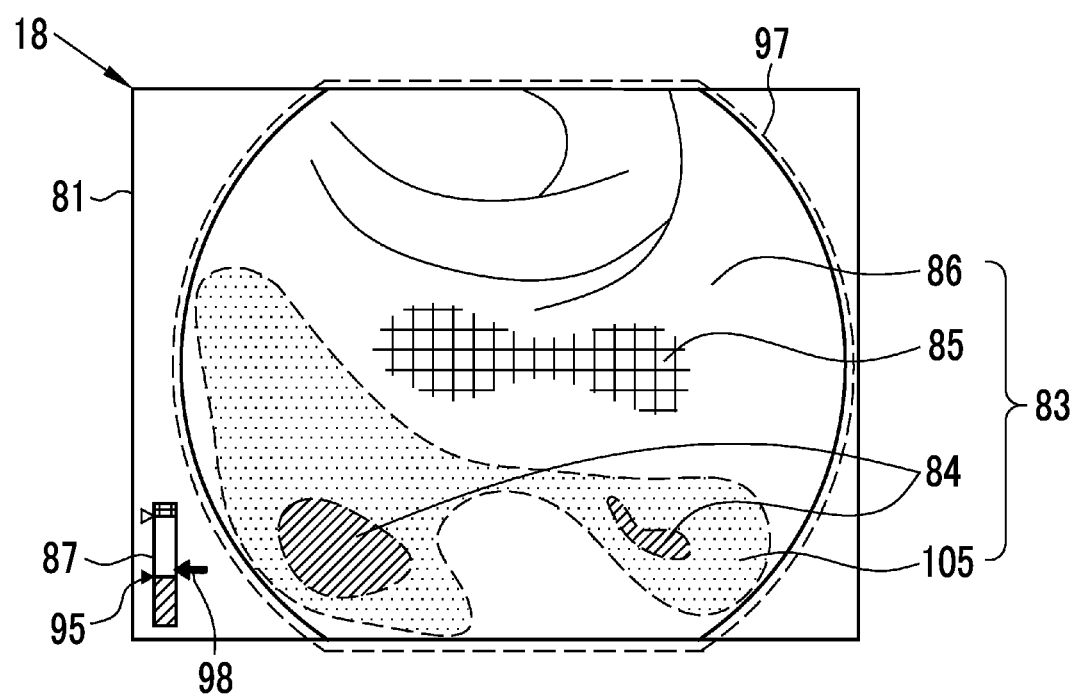
FIG. 14 is an explanatory view illustrating an example of determination performed by an appropriateness determination unit.

The appropriateness determination unit 75 determines that the reference value is not appropriate in a case where the quasi-low value region in which the biological information is higher than the reference value and is equal to or lower than the preset set value is present on the biological information image 83. As shown in FIG. 14, in a case where the quasi-low value region 105 is present on the biological information image 83, the appropriateness determination unit 75 determines that the reference value is not appropriate. In addition, although the quasi-low value region 105 is included in the biological information image 83, the quasi-low value region 105 cannot be visually identified because the quasi-low value region 105 is displayed transparently or colorlessly similar to the other regions in some cases by the reference value color bar 87. Additionally, by looking at the reference value color bar 87, the reference value index 95, and the average value index 98, the average value index 98 is close to the reference value index 95. Therefore, although the average value index 98 is higher than the reference value in the endoscopic image 82, it is possible to estimate that there are many portions where the oxygen saturation is low to the extent that the oxygen saturation is close to the reference value.

In addition, the appropriateness determination unit 75 may determine that the reference value is not appropriate in a case where the quasi-low value region 105 is present on the biological information image 83 in a preset ratio or more. It is preferable that in a case where the area of the quasi-low value region 105 is present in the preset ratio or more with respect to the total area of the biological information image 83 in the biological information image 83, the user confirms the location or distribution of the quasi-low value region 105. In addition, the area of the biological information image 83 is the same as the area of the endoscopic image 82 because the biological information is calculated for the entire endoscopic image 82. By determining that the reference value is not appropriate, the appropriateness determination unit 75 can prompt the user to confirm the quasi-low value region 105 even in a situation where the quasi-low value region 105 is not displayed, and can perform the notification of the determination appropriately.

Figure 15A:
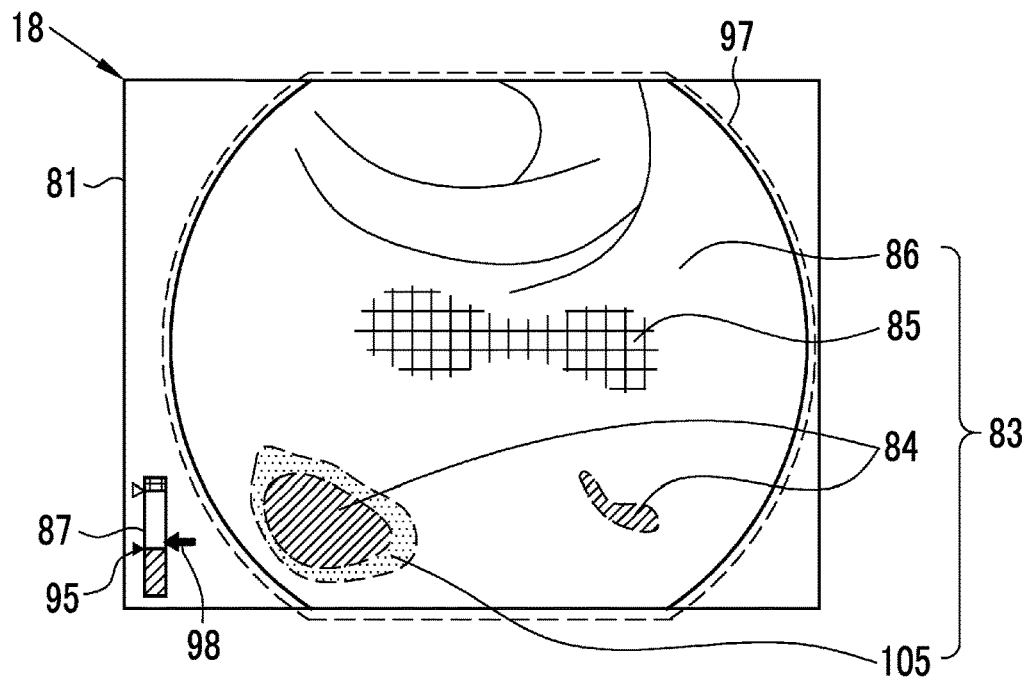
FIGS. 15A and 15B are explanatory views illustrating another example of determination performed by the appropriateness determination unit.
Figure 15B:
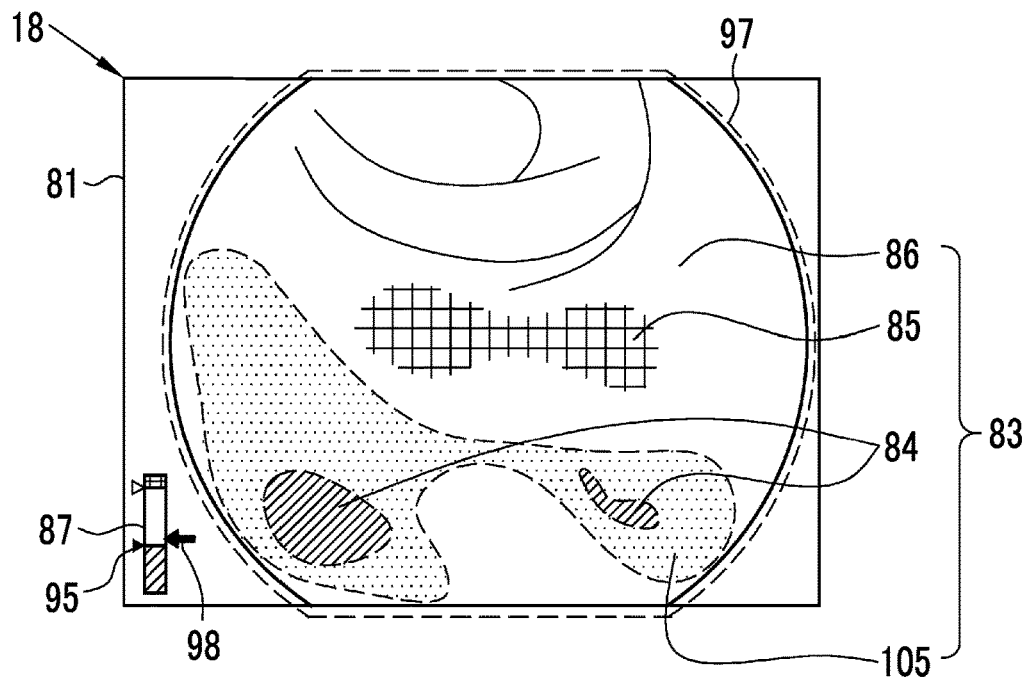

Specifically, for example, in a case where the biological information is the oxygen saturation, the reference value is 40%, and the set value is 50%, and in a case where the area of the quasi-low value region 105 in which the oxygen saturation is higher than 40% and 50% or less is 10% or more of the oxygen saturation image 83, which is a preset value, it is determined that the reference value is not appropriate. As shown in FIGS. 15A and 15B, in FIG. 15A, since the quasi-low value region 105 is less than 10% of the area of the oxygen saturation image 83, the appropriateness determination unit 75 does not determine that the reference value is not appropriate. In addition, the area of the oxygen saturation image 83 is the same as the area of the endoscopic image 82 because the oxygen saturation is calculated for the entire endoscopic image 82. On the other hand, in FIG. 15B, since the quasi-low value region 105 is 10% or more of the area of the oxygen saturation image 83, the appropriateness determination unit 75 determines that the reference value is not appropriate.

The appropriateness determination unit 75 determines the reference value depending on the area ratio of the quasi-low value region 105 occupied in the endoscopic image 82. Accordingly, it is preferable because the determination of the reference value can be set in more detail, and the determination that the reference value is not appropriate can be prevented from being frequently performed and the notification can be performed appropriately.

In addition, the appropriateness determination unit 75 may determine that the reference value is not appropriate in a case where the quasi-low value region 105 continues to be present on the biological information image 83 for a preset time or longer. It is preferable that in a case where the quasi-low value region 105 continues to be present in the biological information image 83, the user confirms the location or distribution of the quasi-low value region 105. Even in a situation where the quasi-low value region 105 is not displayed, the appropriateness determination unit 75 can prompt the user to confirm the quasi-low value region 105 by determining that the reference value is not appropriate, and can perform the notification of the determination appropriately.

Figure 16:
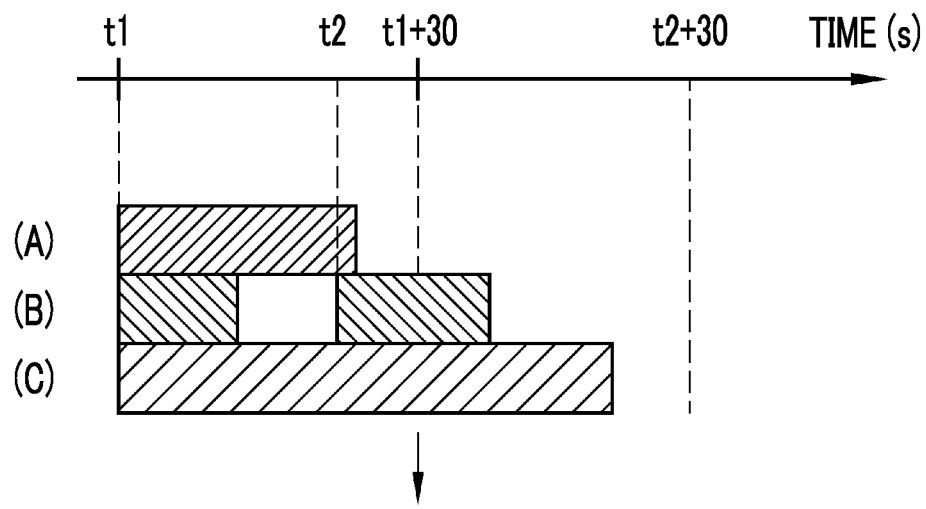
FIG. 16 is an explanatory view illustrating still another example of determination performed by the appropriateness determination unit.

Specifically, for example, in a case where the biological information is the oxygen saturation, the reference value is 40%, and the set value is 50%, and in a case where the area of the quasi-low value region 105 in which the oxygen saturation is higher than 40% and 50% or less is present for 30 seconds or more, which is a preset time, it is determined that the reference value is not appropriate. As shown in FIG. 16, in the case of FIG. 16(A) in which the quasi-low value region 105 starts to be present from a time t1 second and the quasi-low value region 105 does not continues to be present at a time point of time t1+30 seconds, the appropriateness determination unit 75 determines that the reference value is appropriate. On the other hand, in the case of FIG. 16(C) in which the quasi-low value region 105 continues to be present at the time point of time t1+30 seconds, the appropriateness determination unit 75 determines that the reference value is not appropriate. Even in a case where the quasi-low value region 105 is present at the time point of time t1+30 seconds, in a case where the quasi-low value region 105 does not continue for 30 seconds or more, the appropriateness determination unit 75 determines that the reference value is not appropriate. That is, in the case of FIG. 16(B), the quasi-low value region 105 is present at the time point of time t1+30 seconds but the time point when the quasi-low value region 105 has been generated is a time point t2. Therefore, in a case where the quasi-low value region 105 continues to be present until the time point of time t2+30 seconds, the appropriateness determination unit 75 determines that the reference value is not appropriate. However, in the case of FIG. 16(B) in which the quasi-low value region 105 does not continues to be present until the time point of time t2+30 seconds, the appropriateness determination unit 75 does not determine that the reference value is not appropriate. In addition, in FIG. 16, each diagonal line indicates the presence of the quasi-low value region 105.

The appropriateness determination unit 75 determines the reference value on the basis of the duration time of presence of the quasi-low value region 105. Accordingly, it is preferable because the determination of the reference value can be set in more detail, and the determination that the reference value is not appropriate can be prevented from being frequently performed and the notification can be performed appropriately.

In addition, in a case where both the ratio of the quasi-low value region 105 and the duration time of the quasi-low value region 105 in the biological information image 83 are satisfied, the determination that the reference value is not appropriate may be performed. For example, in a case where the reference value is 40% and the set value is 50% in the oxygen saturation, and in a case where the time for which the area of the quasi-low value region 105 in which the oxygen saturation is higher than 40% and 50% or less is present for 10% or more is continuously 30 seconds or more of the oxygen saturation image, it is determined that the reference value is not appropriate. The conditions of the determination are appropriately set in accordance with the situation of the site or the subject. The appropriateness determination unit 75 determines the reference value by using both the area ratio of the quasi-low value region 105 and the duration time of presence of the quasi-low value region 105. Accordingly, it is preferable because the determination of the reference value can be set in more detail, and the determination that the reference value is not appropriate can be prevented from being frequently performed and the notification can be performed appropriately.

In addition, it is preferable that in a case where the appropriateness determination unit 75 determines that the reference value is not appropriate, the reference value setting unit 73 switched and sets the reference value to a higher value. Details such as the width of change in a case where the reference value is switched are appropriately set depending on, for example, the site or the purpose of observation.

Figure 17:
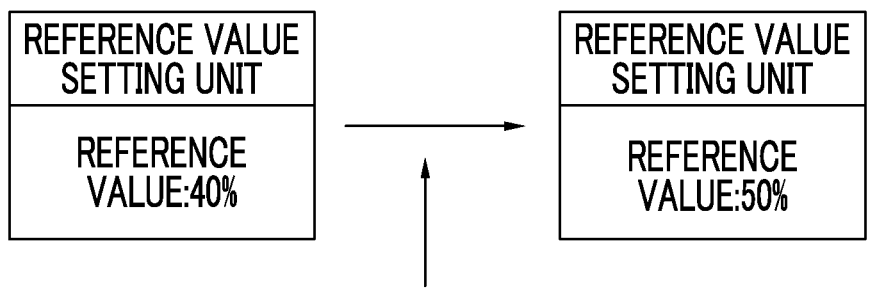
FIG. 17 is an explanatory view illustrating that in a case where the appropriateness determination unit determines that the reference value is not appropriate, the reference value setting unit switches and sets the reference value.

Specifically, as shown in FIG. 17, for example, in a case where the reference value is 40% and the appropriateness determination unit 75 determines that the reference value is not appropriate, the reference value setting unit 73 feeds back the determination of the appropriateness determination unit 75, thereby increasing the reference value by 10%, which is a preset width, from 40%, and switching and setting the reference value to a reference value of 50%.

The reference value setting unit 73 feeds back the determination of the appropriateness determination unit 75 and switches and sets the reference value to a higher value. Accordingly, even in a case where the reference value is too low, it is preferable because the reference value is switched to an appropriate reference value and set to a standard value without any trouble.

In a case where the appropriateness determination unit 75 determines that the reference value is not appropriate, the notification control unit 67 performs a notification regarding the reference value. The notification regarding the reference value is a notification for making the user recognize that the quasi-low value region 105 is present. Therefore, the notification method or notification contents may be any method or contents that the user can recognize the fact. Specifically, for example, the notification is performed by displaying the notification contents on the display 18. In this case, the notification control unit 67 sends information regarding the notification based on the display to the display control unit 66. The display control unit 66 performs control regarding the display.

Figure 18:
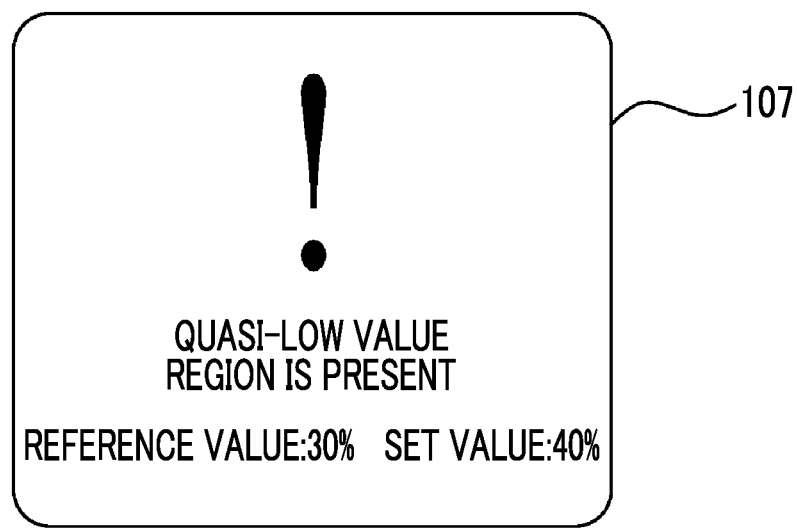
FIG. 18 is an image diagram of a warning display.
Figure 19:
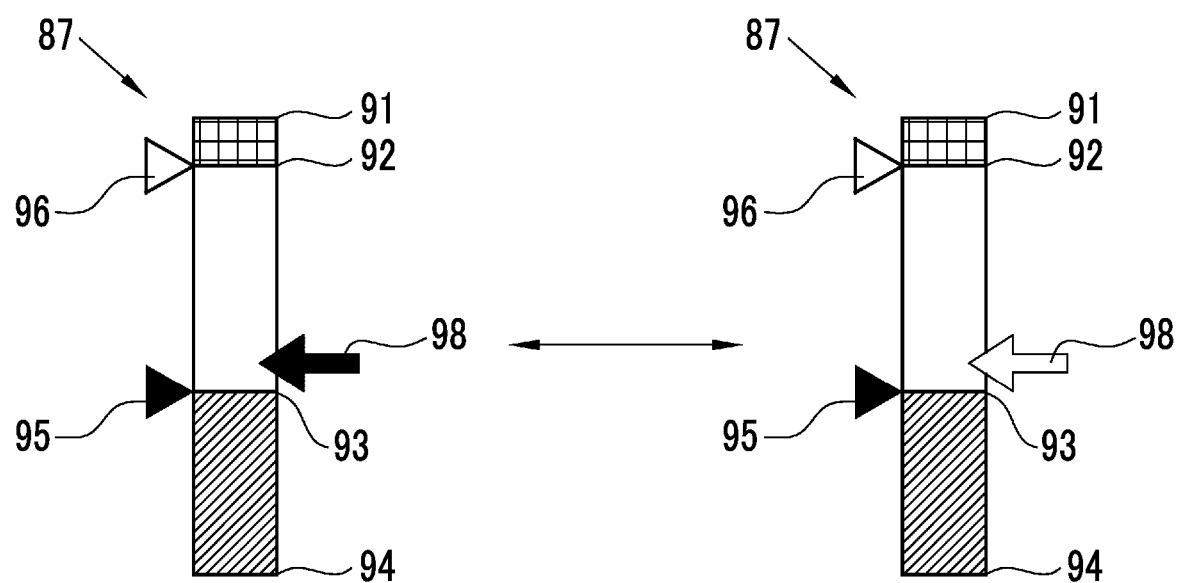
FIG. 19 is an explanatory view illustrating the notification by the reference value color bar combined with the average value index.

The notification contents may be such that the user can recognize that the quasi-low value region 105 is present. As shown in FIG. 18, for example, the notification is performed by displaying the warning display 107 at any point on the display 18. Alternatively, for example, in a case where the reference value color bar 87 is displayed on the display 18, the notification is performed by displaying the average value index 98 in the shape of an arrow on the reference value color bar 87. In a case where the average value index 98 is close to the reference value index 95, the possibility that the quasi-low value region 105 is present is high. Therefore, by displaying the average value index 98 together with the reference value color bar 87, the user can be notified of the presence of the quasi-low value region 105. In addition, the reference value index 95 and the high value index 96 are also displayed on the reference value color bar 87. Alternatively, as shown in FIG. 19, in order to make it difficult to overlook the average value index 98 in the shape of an arrow, for example, the average value index 98 in which the color of the arrow is changed may be displayed by a blinking display in which the average value index is displayed in order every second, or the like.

In addition, in a case where the appropriateness determination unit 75 does not determine that the reference value is not appropriate, the notification control unit 67 may perform the notification that the reference value is appropriate. Regarding the notification, for example, since there is no notification in a case where it is determined that the reference value is not appropriate, the notification that the reference value is appropriate is performed. Additionally, for example, in a case where the reference value is appropriate, the fact is always displayed on the display 18, and in a case where the reference value is no longer appropriate, the display may be changed to a display that warns of the display. Additionally, in a case where the reference value color bar 87 is displayed on the display 18, regarding the arrow-shaped average value index 98 shown on the reference value color bar 87, the user's attention may be attracted by changing the color of the arrow-shaped average value index 98 or changing the size thereof in a case where the reference value is no longer appropriate.

Figure 20:
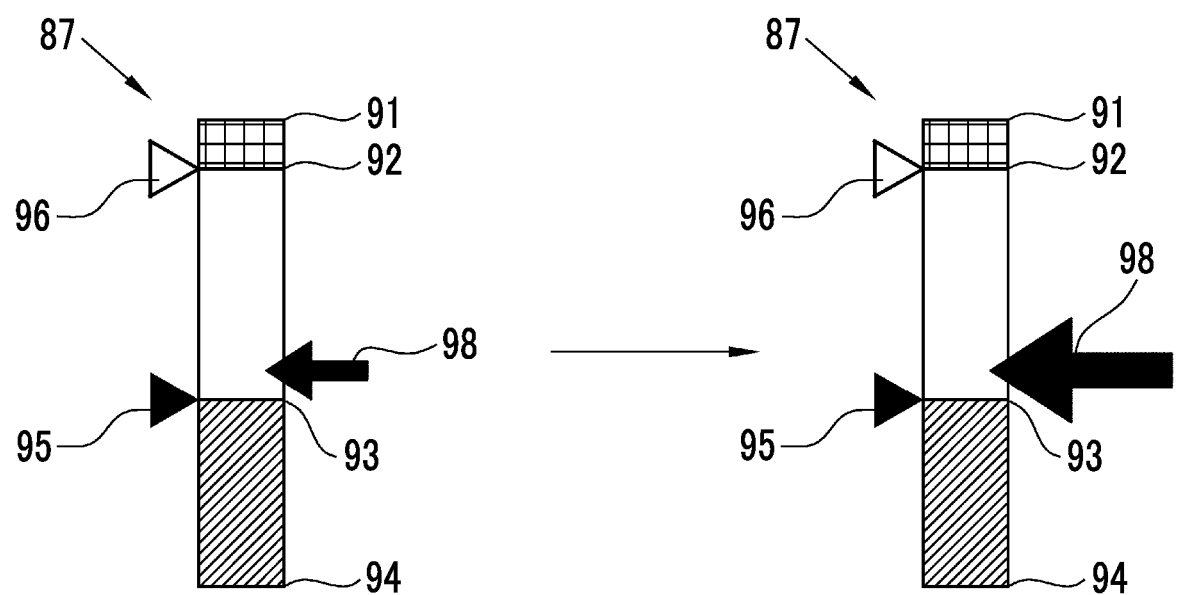
FIG. 20 is an explanatory view illustrating the notification by the reference value color bar combined with arrows.

As shown in FIG. 20, for example, in a case where the arrow-shaped average value index 98 is displayed on the reference value color bar 87, the arrow-shaped average value index 98 is displayed with a normal size in a case where the reference value is appropriate, the arrow-shaped average value index 98 is enlarged and displayed in a case where the reference value is no longer appropriate.

According to the processor device 16 which is the above-described image processing device, in a case where both the endoscopic image 82 and the biological information image 83 are made easy to see by setting the reference value in a case where the biological information is observed by forming the biological information as an image, a notification regarding the reference value is performed in a case where the quasi-low value region 105 that is higher than the reference value and equal to or less than the set value is present. Therefore, it is possible to pay attention to the quasi-low value region 105 without overlooking the quasi-low value region 105. Therefore, the image processing device can prevent overlooking of not only the low value region 84 where the biological information is equal to or lower than the reference value but also the portion of the quasi-low value region 105 where there is a possibility of a lesion or the like, for example, in the observation using the endoscope. In a case where the biological information is lower than the reference value, in the related art, the display that the biological information is lower than the reference value is not performed due to the formation of the biological information as an image. Therefore, for example, in a case where the b is the oxygen saturation, there is a possibility that the user estimates that there is no region where the oxygen saturation is lower.

In particular, for example, in a case where the oxygen saturation of the subject is generally low, and in a case where the reference value is set low in order to observe a region where the oxygen saturation is particularly low, or in a case where the low oxygen region (low value region) 84 that is lower than the reference value disappears due to a change in an observation site or the elapse of time, the display of the low value region 84 is not performed in the oxygen saturation image which is the biological information image 83. However, according to the processor device 16, in a case where there is a quasi-low oxygen region (quasi-low value region) 105 that is higher than the reference value but has a low oxygen saturation, a notification is performed. Therefore, the user can be prevented from not noticing both the low oxygen region 84 and the quasi-low value region 105, which are specific regions regarding the oxygen saturation.

Additionally, in a case where the notification regarding the reference value is performed, the user can change the reference value immediately. The reference value can be easily changed, for example, in 1% increments with the keyboard 19, the scope button 12 *g*, the foot switch (not shown), or the like. Therefore, in a case where the reference value is changed, the reference value can be changed quickly and flexibly without burdening the user. Additionally, in a case where the reference value is changed, the reference value correspondence information based on the reference value or various correspondence information such as the reference value color bar 87 is automatically changed. Therefore, the user can perform the observation with an appropriate setting or display without any trouble, and the biological information can be prevented from being overlooked in a specific region.

Figure 21:
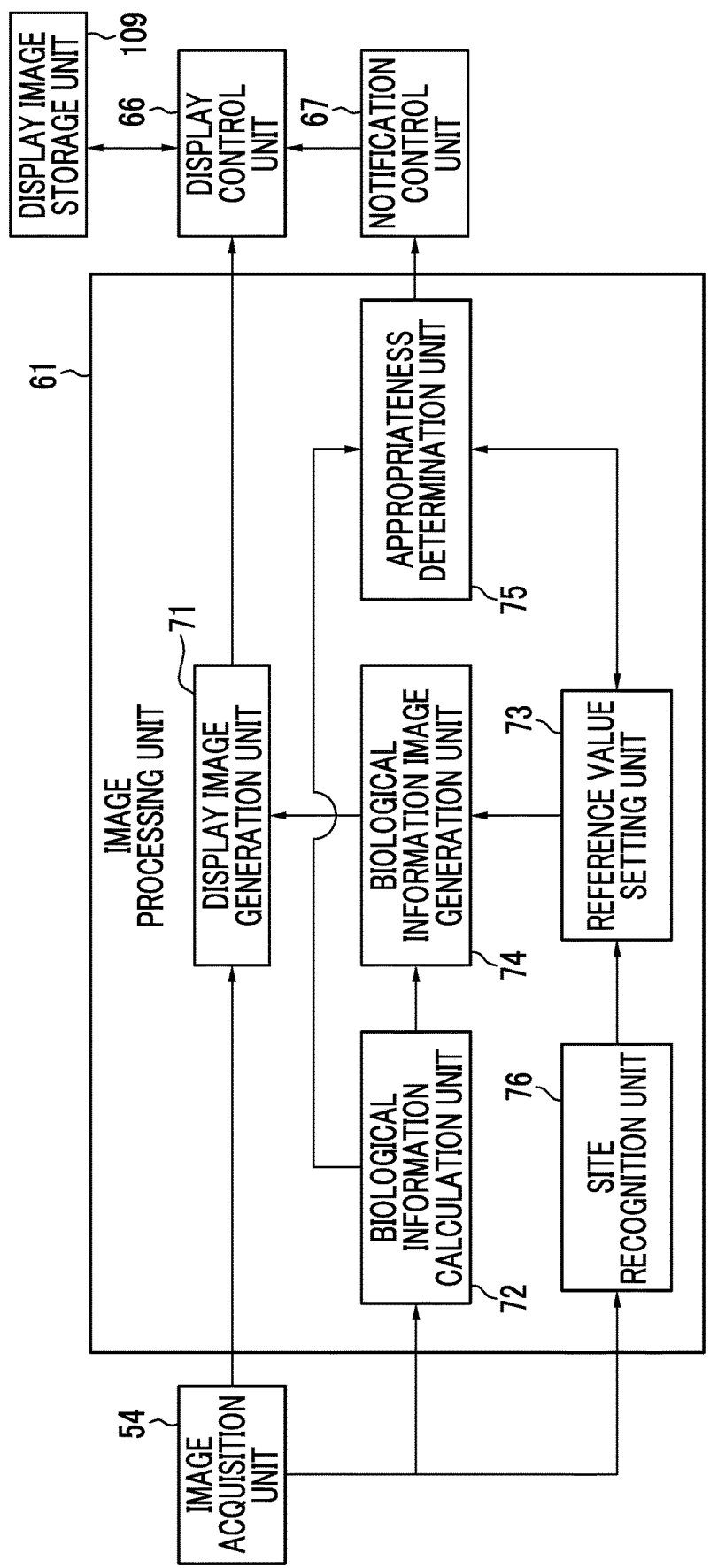
FIG. 21 is a block diagram of the image processing unit connected to a display image storage unit.

In addition, it is preferable that the processor device 16 comprises the display image storage unit 109 that is connected to the display 18 displaying the display image 81 and stores the display image 81, and the display control unit 66 that performs the control of thumbnail-displaying the stored display image 81 as thumbnails on the display 18. Moreover, as shown in FIG. 21, the processor device further comprises the display image storage unit 109. The display image 81 generated by the display image generation unit 71 is stored by the display image storage unit 109.

The display control unit 66 performs the control of thumbnail-displaying one or a plurality of display images 81 stored by the display image storage unit 109 on the display 18 in accordance with preset conditions. The preset conditions are, for example, selected from all of the display images 81 displayed from the past to the present for a predetermined period on the basis of the preset criteria. In a case where the display image 81 is created for each frame, for example, one display image 81 is selected every 30 seconds, and four display images 81 selected from the past 30 seconds to the past 2 minutes are thumbnail-displayed as thumbnails. In a case where a new display image 81 is generated, the oldest display image 81 among the display images 81 thumbnail-displayed on the display 18 is deleted, and the new display image 81 is displayed instead, and this is repeated every 30 seconds. In this case, changes in the biological information can be displayed in time series during the observation using the endoscope.

Figure 22:
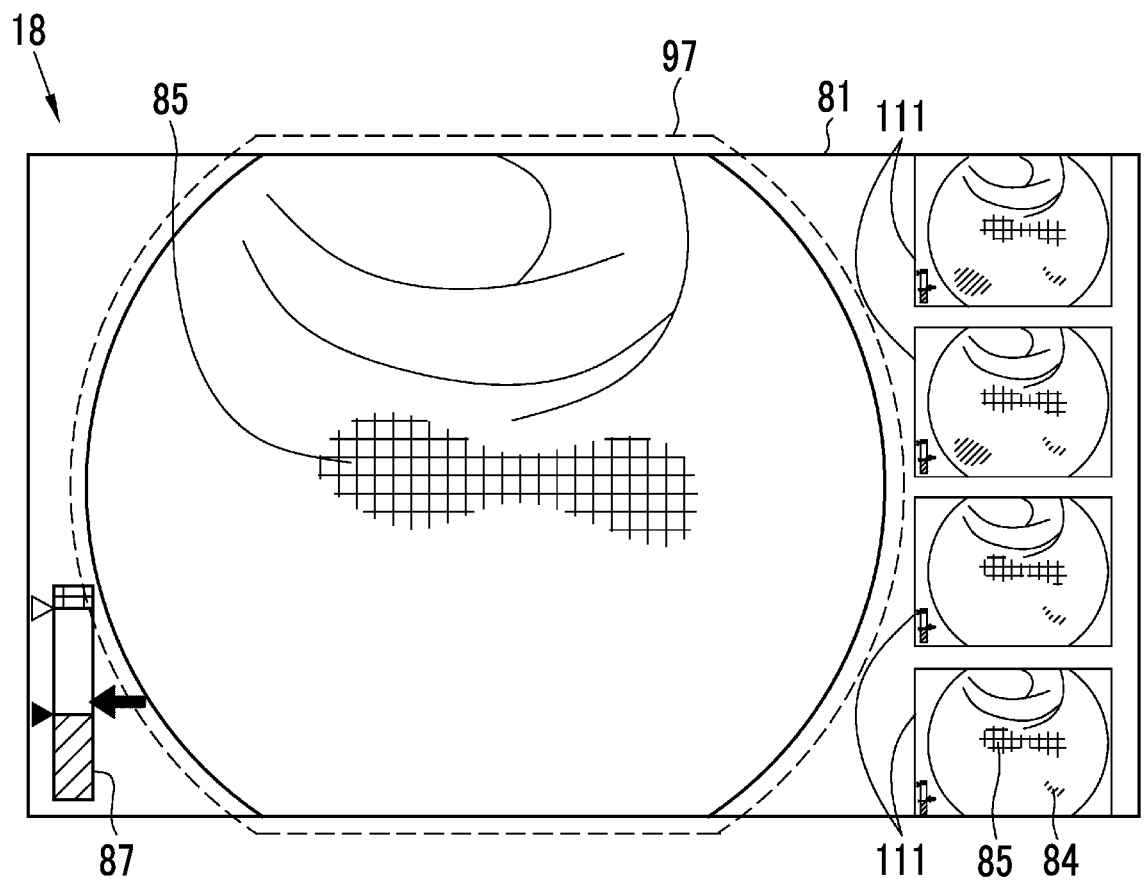
FIG. 22 is an explanatory view illustrating thumbnail display of display images.

As shown in FIG. 22, specifically, for example, in a case where four display images 81 are selected every 30 seconds, and thumbnail images 111 selected from the past 30 seconds to the past 2 minutes are displayed, the thumbnail images 111 30 seconds ago, 1 minute ago, 1 minute 30 seconds ago, and 2 minutes ago are displayed in a new order from the top on the right side of the display image 81 currently being observed. In addition, in FIG. 22, only some of the reference numerals are given in order to avoid the complexity of the drawings.

Additionally, the preset condition is, for example, a past display image 81 at the same site of the same patient. In this case, the comparison of the biological information in the same site or the like can be performed easily. For example, in the same patient, changes in the oxygen saturation before and after anastomosis of the stomach can be displayed on the same display 18. Additionally, for example, the display images 81 selected from the display image storage unit 109 at regular time intervals may be thumbnail-displayed by using acquisition time information included in the endoscopic image 82.

Additionally, in the past plurality of display images 81 to be thumbnail-displayed, the display images 81 may be the biological information image 83 in which the biological information is shown in pseudo color. The pseudo color is one of the methods of forming the biological information as an image, and is obtained by displaying different colors in accordance with the biological information on the basis of the biological information calculated for each pixel of the endoscopic image 82. This method is referred to as the pseudo color because a pseudo color different from the color shown by natural observation in the endoscopic image is used. In order to display the biological information in the pseudo color, for example, there are a method of using the color correspondence information (color table), a method of applying different gains to a spectral image of the endoscopic image in accordance with the biological information, and the like. The color correspondence information is correspondence information in which different colors are associated with each other in accordance with the biological information. In the present embodiment, since the biological information is the oxygen saturation, the color correspondence information is pseudo color correspondence information in which different colors are associated with each other in accordance with the oxygen saturation, and the range of the oxygen saturation is, for example, pseudo color correspondence information corresponding to respective color colors from blue to red.

The pseudo color correspondence information can be set in accordance with the type of the subject of the biological information image, the purpose of observation, and the like. For example, 1% of the oxygen saturation from 0% to 100% is used as the pseudo color correspondence information associated with each color of each stage in 101 stages from blue to red. Therefore, the pseudo color correspondence information is correspondence information in which the measured value of the oxygen saturation and the color are associated with each other, and the value of the oxygen saturation and the color are associated with each other on a one-to-one basis. Accordingly, in the oxygen saturation image which is a biological information image, the color corresponding to the measured value of the oxygen saturation can be displayed for each pixel. Therefore, in the thumbnail images, the color corresponding to the absolute measured value of the oxygen saturation is displayed. Therefore, the oxygen saturation can be compared between the images, and an absolute change in the oxygen saturation can be identified easily.

In addition, it is preferable that in a case where the reference value setting unit 73 sets the reference value, the display control unit 66 performs the control of displaying the display image 81 to be thumbnail-displayed on the display after changing the display image on the basis of the reference value. The display image generation unit 71 generates the reference value color correspondence information in a case where the reference value setting unit 73 sets the reference value. Then, in a case where the reference value color correspondence information is generated for the biological information image 83 included in the thumbnail-displayed display image 81, the biological information image 83 based on the reference value color correspondence information is generated. The display image generation unit 71 may store the biological information image 83 included in the display image 81 to be thumbnail-displayed, or may acquire the display image 81 stored in the display image storage unit 109. The display image generation unit 71 generates the biological information image 83 included in the thumbnail-displayed display image 81 again, and also generates the display image 81 again. In the generated display image 81, the biological information image 83 is changed in response to a change in the reference value. As soon as the display image 81 is generated, the display image 81 is thumbnail-displayed again on the display. Additionally, in a case where the generated display image 81 is stored, for example, in the display image storage unit 109, and in a case where the display image 81 including the same acquisition time in the endoscopic image 82 included in the display image 81 is stored, the past display image 81 is updated and stored. In a case where the reference value is changed in this way, the thumbnail-displayed display image 81 is also changed in accordance with the changed reference value and displayed again.

In a case where the past display image 81 is thumbnail-displayed, the reference value is changed or the thumbnail-displayed display image is also displayed on the basis of the changed reference value. Accordingly, in all of the display images 81 to be displayed on the display 18, it is preferable because the display images 81 can be compared between the images by a single reference value and a change in the oxygen saturation is identified easily.

In addition, as in the present embodiment, it is preferable that the biological information is the oxygen saturation of the subject. Since the biological information is the oxygen saturation, the oxygen saturation can be efficiently observed using the reference value in the subject. It is known that there is a possibility that a region having a low oxygen saturation in the subject is a lesion, a suture failure of the intestinal tract, or the like. Therefore, since the biological information is the oxygen saturation, this is effective for observation, examination, or diagnosis with the endoscope.

Additionally, although the low value region 84 equal to or lower than the reference value of the biological information and the quasi-low value region 105 have been described above, the same applies to the high value region equal to or higher than the reference value of the biological information and a quasi-high value region.

Figure 23:
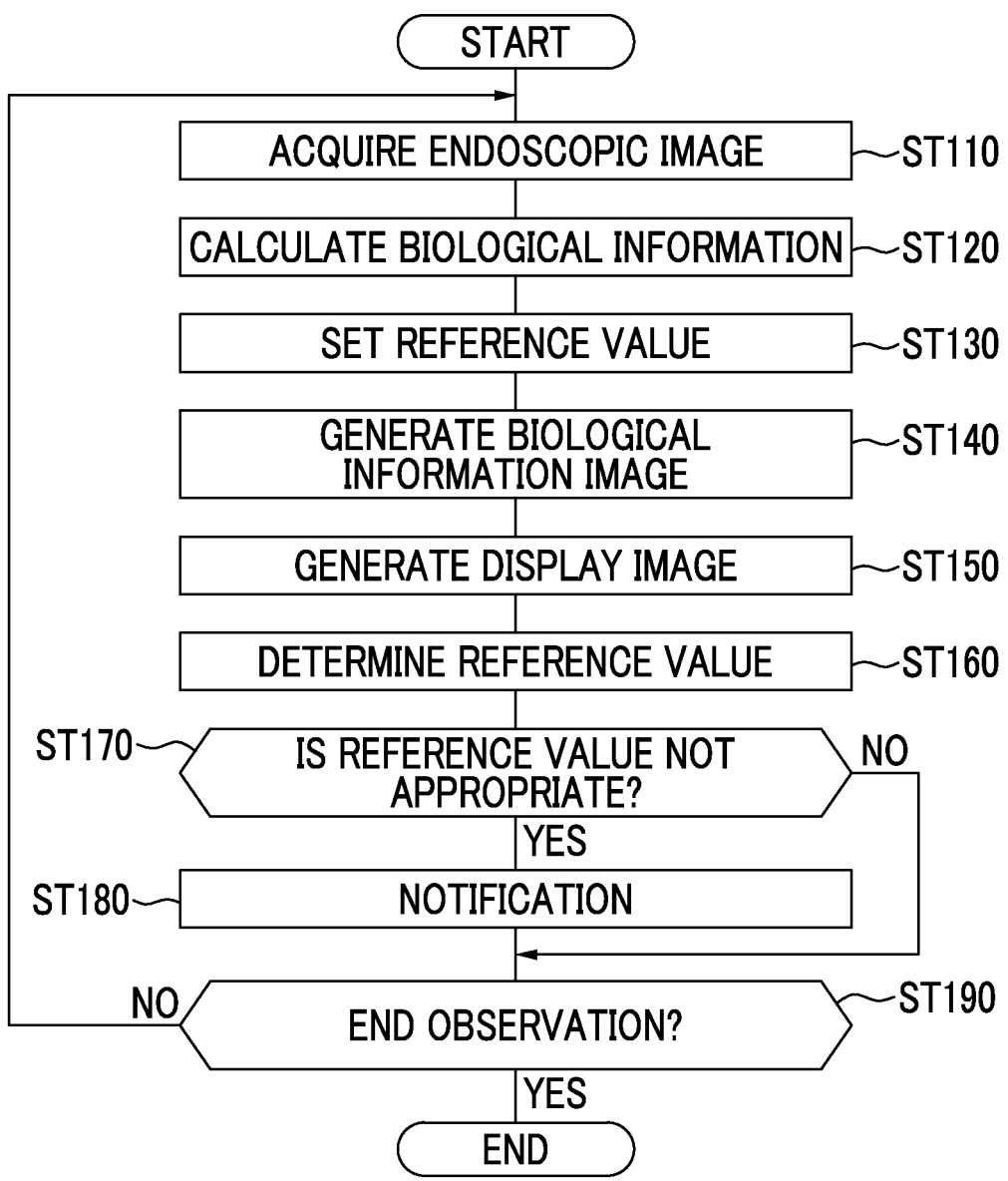
FIG. 23 is a flowchart for explaining a series of flows performed by an image processing device.

Next, a series of processing performed by the image processing device will be described with reference to a flowchart shown in FIG. 23. In a case where the observation is started, the endoscopic image 82 is acquired (Step ST110), and the biological information is calculated on the basis of the acquired endoscopic image 82 (Step ST120). The reference value setting unit 73 sets the reference value (Step ST130). The biological information image is generated on the basis of the reference value (Step ST140). The display image is generated on the basis of the biological information image (Step ST150). The determination unit determines the reference value (Step ST160), and in a case where the determination result indicates that the reference value is not appropriate (YES in Step ST170), a notification is performed (Step ST180). In a case where there is no determination result that the reference value is not appropriate (NO in Step ST170), the notification is not performed. In a case where the observation is completed (YES in Step ST190), the series of flows is completed. In a case where the observation is continued (NO in Step ST190), the process returns to the acquisition of the endoscopic image 82.

In addition, in the above embodiment, the present invention is applied to the endoscope system that processes the endoscopic image 82. However, the present invention can be applied to a medical image processing system that processes a medical image other than the endoscopic image 82, in a case where a still image is stored.

Figure 24:
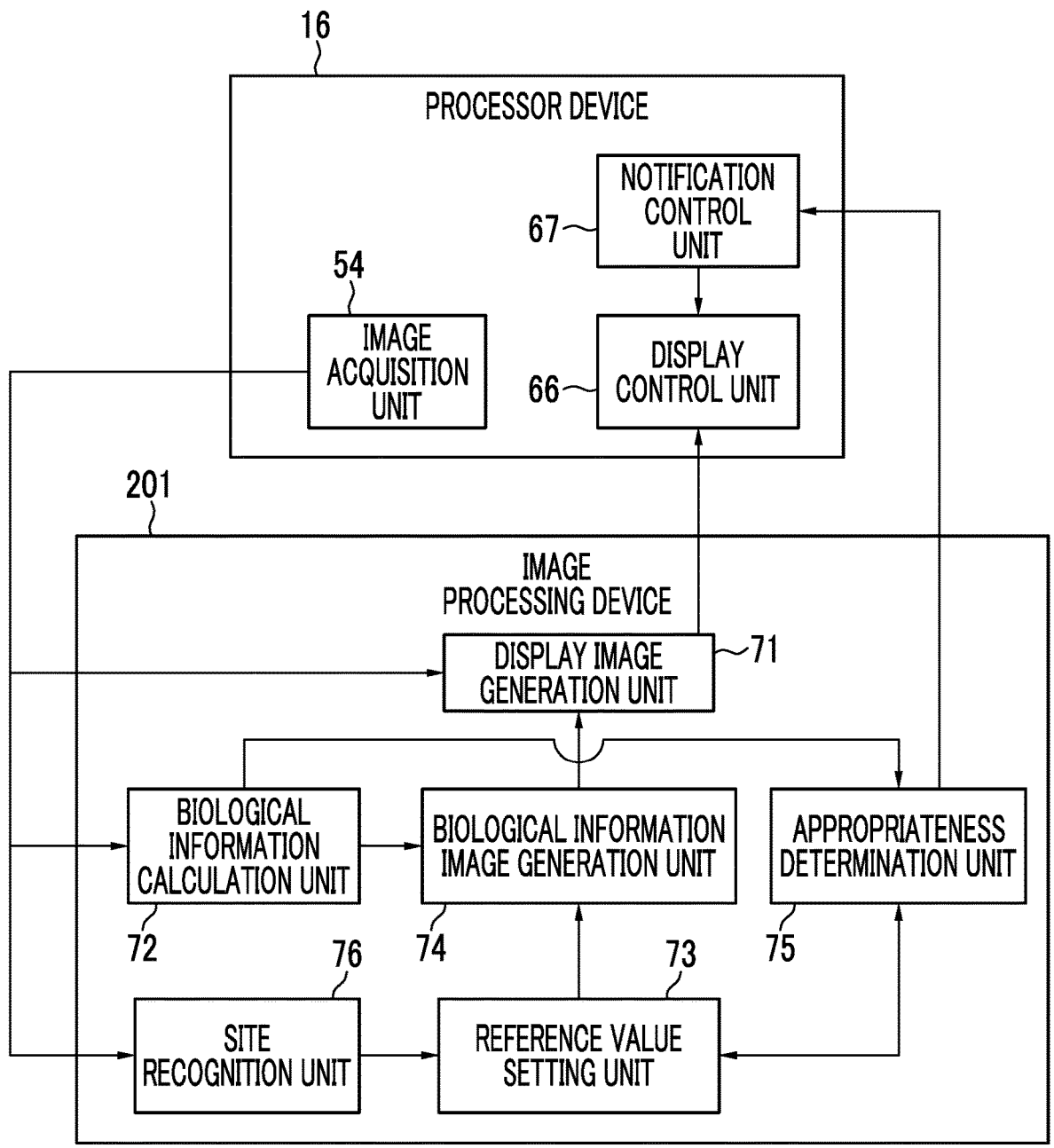
FIG. 24 is a block diagram of an image processing device separate from a processor device.

In the above-described embodiment and modification examples, the processor device 16 functions as the image processing device. However, as shown in FIG. 24, the image processing unit 61 can provide an image processing device 201 comprising the display image generation unit 71, the biological information calculation unit 72, the reference value setting unit 73, the biological information image generation unit 74, the appropriateness determination unit 75, and the site recognition unit 76 separately from the processor device 16.

Figure 25:
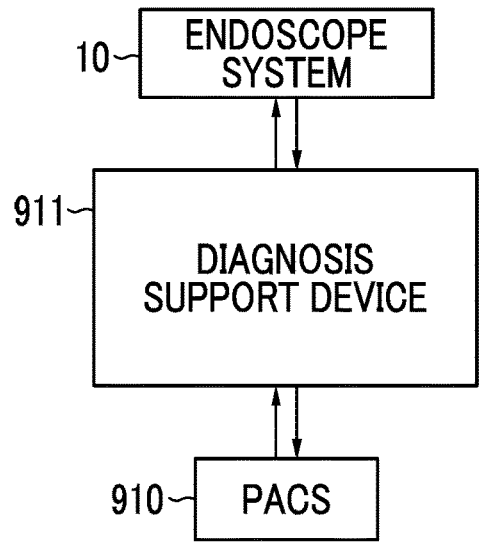
FIG. 25 is an explanatory view showing a diagnosis support device.
Figure 26:
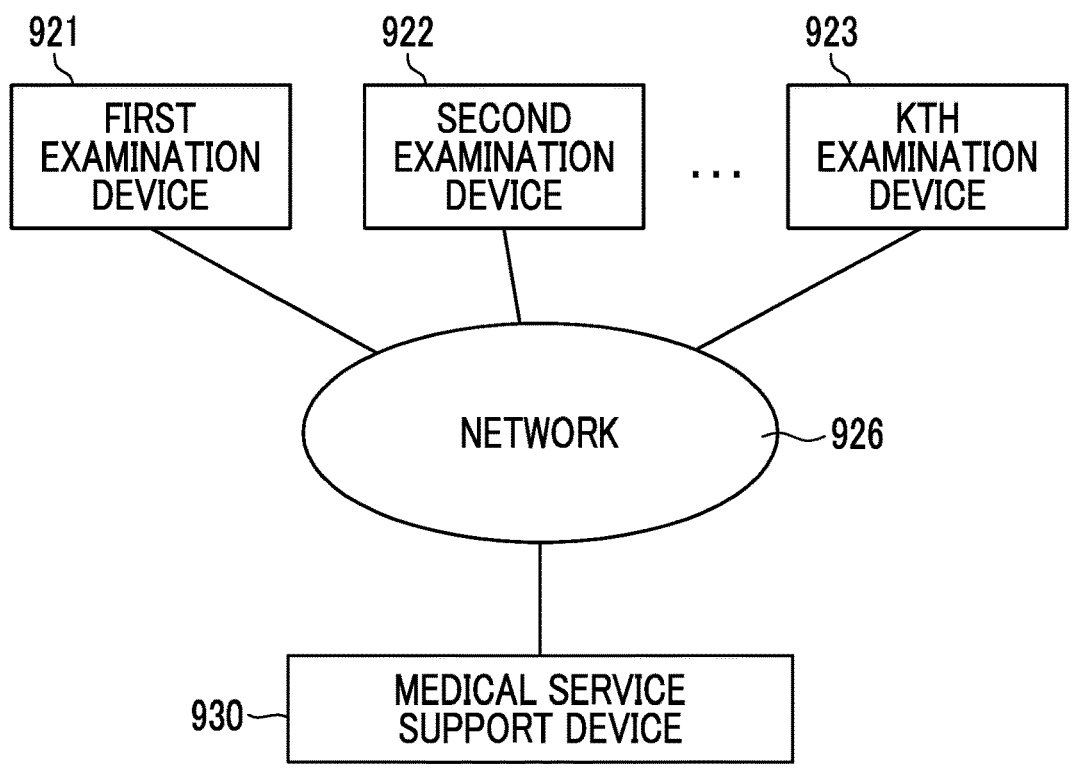
FIG. 26 is an explanatory view showing a medical service support device.

In addition, as shown in FIG. 25, the display image generation unit 71, the biological information calculation unit 72, the reference value setting unit 73, the biological information image generation unit 74, the appropriateness determination unit 75, and the site recognition unit 76 can be provided in, for example, a diagnosis support device 911 that acquires a RAW image captured by the endoscope 12, directly from the endoscope system 10 or indirectly from a picture archiving and communication systems (PACS) 910. Additionally, as shown in FIG. 26, the display image generation unit 71, the biological information calculation unit 72, the reference value setting unit 73, the biological information image generation unit 74, the appropriateness determination unit 75, and the site recognition unit 76 may be provided in a medical service support device 930 that is connected various examination devices, such as a first examination device 921, a second examination device 922, . . . , a Kth examination device 923, and the like, including the endoscope system 10, via a network 926.

The above embodiment and modification examples can be optionally carried out in any combination of some or all thereof. Additionally, in the above embodiment and modification examples, the so-called flexible endoscope having the flexible insertion part 12a is used as the endoscope 12. However, the present invention is also suitable in a case where a capsule type endoscope swallowed and used by the subject or a rigid endoscope (laparoscope) used for surgery or the like is used, is used.

The above-described embodiment and modification examples are method of operating an image processing device comprising an image processor, and the image processor includes a method of operating the image processing device that acquires an endoscopic image obtained by imaging a subject with an endoscope, calculates biological information on the basis of the endoscopic image, sets a reference value of the biological information, generates a biological information image obtained by forming the biological information as an image so that a low value region equal to or lower than the reference value and the other region are distinguishable from each other, generates a display image in which the biological information image is superimposed on the endoscopic image, determines that the reference value is not appropriate in a case where a quasi-low value region in which the biological information is higher than the reference value and equal to or lower than a preset set value is present in the biological information image, and performs a notification regarding the reference value in a case where it is determined the reference value is not appropriate.

In the above embodiment, the hardware structure of a processing unit that executes various kinds of processing such as the control unit 52, the image acquisition unit 54, the DSP 56, the noise reduction unit 58, the conversion unit 59, the image processing unit 61, the display control unit 66, and the notification control unit 67 included in the processor device 16 is various processors as shown below. The various processors include a central processing unit (CPU) that is a general-purpose processor that executes software (programs) to function as various processing units, a programmable logic device (PLD), which is a processor capable of changing the circuit configuration after manufacturing, such as a field programmable gate array (FPGA), a dedicated electric circuit that is a processor having a circuit configuration designed in a dedicated manner to execute various processing, and the like.

One processing unit may be constituted of one of the various processors, or may be constituted of a combination (for example, a plurality of FPGAs or a combination of a CPU and an FPGA) of two or more processors of the same type or different types. Additionally, a plurality of processing units may be constituted of one processor. As an example in which the plurality of processing units is constituted of one processor, firstly, as represented by a computer such as a client or a server, there is a form in which one processor is configured by a combination of one or more CPUs and software and this processor functions as the plurality of processing units. Secondly, as represented by system on chip (SoC), there is a form in which a processor that realizes the functions of the entire system including a plurality of processing units with one integrated circuit ((IC) chip is used. In this way, the various processing units are configured using one or more of the various processors as the hardware structure.

Moreover, the hardware structure of the various processors is, more specifically, an electric circuit (circuitry) in a form in which circuit elements such as semiconductor elements are combined together.

In addition, in addition to the endoscope system that acquires endoscopic images, the processor device, and the other related devices, the present invention can also be used in systems or devices that acquire medical images (including moving images) other than the endoscopic images. For example, the present invention can be applied to ultrasonic examination devices, X-ray image capturing devices (including computed tomography (CT) examination devices, mammography devices, or the like), magnetic resonance imaging (MRI) devices, and the like.

EXPLANATION OF REFERENCES

10: endoscope system
12: endoscope
12a: insertion part
12b: operating part
12c: bendable part
12d: distal end part
12e: angle knob
12f: treatment tool insertion port
12g: scope button
13: zoom operation part
14: light source device
16: processor device
18: display
19: keyboard
20: light source unit
20a: V-LED
20b: B-LED
20c: G-LED
20d: R-LED
22: light source control unit
30a Illumination optical system
30b: imaging optical system
45: illumination lens
46: objective lens
47: zoom lens
48: image sensor
52: control unit
54: image acquisition unit
56: DSP
58: noise reduction unit
59: conversion unit
61: image processing unit
66: display control unit
67: notification control unit
71: display image generation unit
72: biological information calculation unit
73: reference value setting unit
74: biological information image generation unit
75: appropriateness determination unit
76: site recognition unit
81: display image
82: endoscopic image
83: biological information image (oxygen saturation image)
84: low value region (low oxygen region)
85: high value region
86: intermediate region
87: reference value color bar
91 to 94: scale
95: reference value index
96: high value index
97: superimposed image
98: average value index
101a, 101b: slide bar
102a, 102b: slider
105: quasi-low value region (quasi-low oxygen region)
107: warning display
109: display image storage unit
111: thumbnail image
201: image processing device
910: PACS
911 diagnosis support device
921: first examination device
922: second examination device
923: Kth examination device
926: network
930: medical service support device
ST110 to ST190: step

What is claimed is:
1. An image processing device comprising:
an image processor configured to:
acquire an endoscopic image obtained by imaging a subject with an endoscope;
calculate biological information on the basis of the endoscopic image;
set a reference value of the biological information;
generate a biological information image obtained by forming the biological information as an image so that a low value region equal to or lower than the reference value and the other region are distinguishable from each other;
generate a display image in which the biological information image is superimposed on the endoscopic image;
determine that the reference value is not appropriate in a case where a quasi-low value region in which the biological information is higher than the reference value and equal to or lower than a preset set value is present in the biological information image; and perform a notification regarding the reference value in a case where it is determined the reference value is not appropriate.

2. The image processing device according to claim 1, wherein the image processor is further configured to generate reference value color correspondence information in which a region where the biological information is equal to or lower than the reference value is associated with a specific color, and generate the biological information image on the basis of the reference value color correspondence information.

3. The image processing device according to claim 2, wherein the image processor is further configured to generate a display image by using a reference value color bar obtained by forming the reference value color correspondence information as an image, and a reference value index indicating the reference value.

4. The image processing device according to claim 3, wherein the image processor is further configured to, in a case where the reference value is set, generate the display image by using the reference value index indicating the set reference value.

5. The image processing device according to claim 3, wherein the image processor is further configured to calculate an average value of the biological information in the endoscopic image, and generate the display image by using the reference value color bar and an average value index indicating the average value.

6. The image processing device according to claim 1, wherein the image processor is further configured to, in a case where the reference value is set, generate reference value color correspondence information on the basis of the set reference value.

7. The image processing device according to claim 1, wherein the image processor is connected to a display that displays the display image and a display image storage that stores the display image, and
the image processor is further configured to perform a control of thumbnail-displaying the display image stored in the display image storage on the display.

8. The image processing device according to claim 7, wherein the image processor is further configured to, in a case where the reference value is set, perform a control of displaying the display image to be thumbnail-displayed on the display after changing the display image on the basis of the reference value.

9. The image processing device according to claim 1, wherein the image processor is further configured to, in a case where the quasi-low value region is present in a preset ratio or more in the biological information image, determine that the reference value is not appropriate.

10. The image processing device according to claim 1, wherein the image processor is further configured to, in a case where the quasi-low value region continues to be present for a preset time or more, determine that the reference value is not appropriate.

11. The image processing device according to claim 1, wherein the image processor is further configured to, in a case where it is not determined that the reference value is not appropriate, perform a notification that the reference value is appropriate.

12. The image processing device according to claim 1, wherein the image processor is further configured to recognize a site of the subject on the basis of the endoscopic image, and set the reference value on the basis of the site.

13. The image processing device according to claim 1, wherein the image processor is further configured to, in a case where the image processor determines that the reference value is not appropriate, switch and set the reference value to a higher value.

14. The image processing device according to claim 1, wherein the image processor is further configured to, in a case where the reference value and the set value satisfy a preset condition, change and set the reference value to a preset value that is higher than the reference value before a change and does not exceed the set value.

15. The image processing device according to claim 1, wherein the biological information is an oxygen saturation of the subject.

16. A method of operating an image processing device including an image processor, the method comprising:
acquiring an endoscopic image obtained by imaging a subject with an endoscope;
calculating biological information on the basis of the endoscopic image;
setting a reference value of the biological information;
generating a biological information image obtained by forming the biological information as an image so that a low value region equal to or lower than the reference value and the other region are distinguishable from each other;
generating a display image in which the biological information image is superimposed on the endoscopic image;
determining that the reference value is not appropriate in a case where a quasi-low value region in which the biological information is higher than the reference value and equal to or lower than a preset set value is present in the biological information image; and
performing a notification regarding the reference value in a case where it is determined the reference value is not appropriate.

* * * * *